(12) United States Patent
Hashida et al.

(10) Patent No.: US 9,982,622 B2
(45) Date of Patent: May 29, 2018

(54) CONTROL SYSTEM AND CONTROL METHOD FOR INTERNAL COMBUSTION ENGINE

(71) Applicant: TOYOTA JIDOSHA KABUSHIKI KAISHA, Toyota-shi, Aichi-ken (JP)

(72) Inventors: Tatsuhiro Hashida, Shizuoka-ken (JP); Kazuhiro Wakao, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 101 days.

(21) Appl. No.: 15/119,497

(22) PCT Filed: Feb. 16, 2015

(86) PCT No.: PCT/IB2015/000159
§ 371 (c)(1),
(2) Date: Aug. 17, 2016

(87) PCT Pub. No.: WO2015/124985
PCT Pub. Date: Aug. 27, 2015

(65) Prior Publication Data
US 2017/0009695 A1 Jan. 12, 2017

(30) Foreign Application Priority Data

Feb. 20, 2014 (JP) ................. 2014-030969

(51) Int. Cl.
*F01N 3/00* (2006.01)
*F02D 41/26* (2006.01)
(Continued)

(52) U.S. Cl.
CPC ....... *F02D 41/263* (2013.01); *F02D 41/1444* (2013.01); *F02D 41/1454* (2013.01);
(Continued)

(58) Field of Classification Search
USPC .................. 60/274, 276, 277, 286, 297, 301
See application file for complete search history.

(56) References Cited

U.S. PATENT DOCUMENTS 5,145,566 A  9/1992 Logothetis et al.
6,051,123 A  4/2000 Joshi et al.
(Continued)

FOREIGN PATENT DOCUMENTS

EP   0982586 A2   3/2000
JP   H02-122255 A  5/1990
(Continued)

*Primary Examiner* — Binh Q Tran
(74) *Attorney, Agent, or Firm* — Hunton Andrews Kurth LLP

(57) ABSTRACT

A control system for an engine includes a limiting current gas sensor includes a pumping cell arranged in the exhaust passage of the engine and an ECU. The ECU is configured to: execute step-up operation for increasing a voltage applied between a pair of electrodes of the pumping cell from a first voltage to a second voltage, then, execute step-down operation for reducing the applied voltage from the second voltage to a third voltage within a second period; acquire an air-fuel ratio of the exhaust gas multiple times within a first period from a start of the step-up operation to a start of the step-down operation; acquire a first waveform characteristic value indicating a characteristic of a waveform of current within the second period; and estimate an actual concentration of sulfur in fuel by using the first waveform characteristic value and the acquired air-fuel ratios.

14 Claims, 20 Drawing Sheets

(51) Int. Cl.
    *F02D 41/14*     (2006.01)
    *G01N 27/407*     (2006.01)
    *G01N 33/28*     (2006.01)
    *F02D 41/18*     (2006.01)

(52) U.S. Cl.
    CPC ..... *F02D 41/1456* (2013.01); *G01N 27/4074* (2013.01); *F02D 41/1458* (2013.01); *F02D 41/18* (2013.01); *F02D 2200/0612* (2013.01); *G01N 33/287* (2013.01)

(56) References Cited

U.S. PATENT DOCUMENTS

| | | | |
|---|---|---|---|
| 6,340,419 | B1 | 1/2002 | Nakae et al. |
| 9,599,055 | B2 * | 3/2017 | Kitaura ............... F02D 41/1439 |
| 9,732,659 | B2 * | 8/2017 | Mizutani ............... F01N 11/007 |
| 9,753,005 | B2 * | 9/2017 | Kato ................ G01N 27/4074 |
| 2009/0165440 | A1 | 7/2009 | Sawada et al. |
| 2016/0108844 | A1 * | 4/2016 | Nishioka ............... F01N 3/2066 60/285 |
| 2016/0209353 | A1 * | 7/2016 | Aoki ................ G01N 27/4074 |

FOREIGN PATENT DOCUMENTS

| | | |
|---|---|---|
| JP | 2000-065782 A | 3/2000 |
| JP | 2004-069547 A | 3/2004 |
| JP | 4664882 B2 | 4/2011 |
| JP | 2015-017932 A | 1/2015 |
| JP | 2015-036538 A | 2/2015 |
| JP | 2015-155666 A | 8/2015 |
| WO | 2015/022568 A1 | 2/2015 |

\* cited by examiner

| AIR-FUEL RATIO AF | CORRECTION COEFFICIENT Ks |
|---|---|
| 15 | 1.31 |
| 20 | 1.00 |
| 25 | 0.81 |
| 30 | 0.68 |
| 35 | 0.58 |

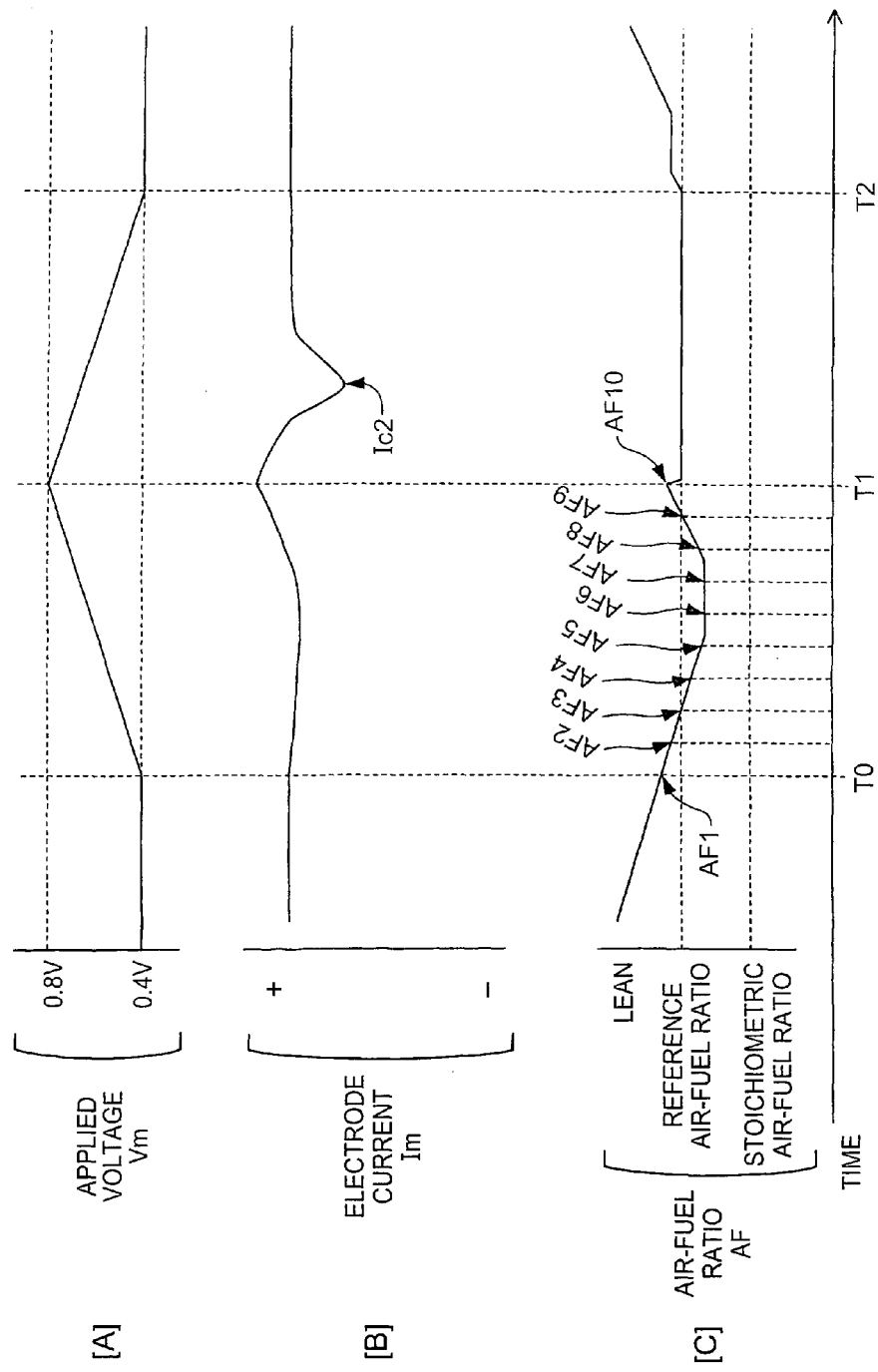

CONTROL SYSTEM AND CONTROL METHOD FOR INTERNAL COMBUSTION ENGINE

CROSS-REFERENCE TO RELATED APPLICATIONS

This is a national phase application based on the PCT International Patent Application No. PCT/IB2015/000159 filed Feb. 16, 2015, claiming priority to Japanese Patent Application No. 2014-030969 filed Feb. 20, 2014, the entire contents of both of which are incorporated herein by reference.

BACKGROUND OF THE INVENTION

1. Field of the Invention

The invention relates to a control system and control method for an internal combustion engine, which are able to estimate the concentration of sulfur in fuel of the internal combustion engine with the use of a limiting current gas sensor.

2. Description of Related Art

There is known a limiting current gas sensor as a gas sensor that is arranged in an exhaust passage of an engine. The limiting current gas sensor includes a pumping cell. The pumping cell includes a solid electrolyte and a pair of electrodes. The solid electrolyte layer has ion conductivity. The pair of electrodes are respectively fixed to both faces of the solid electrolyte layer. One of the pair of electrodes is exposed to a test gas (that is, exhaust gas) that is introduced through a diffusion-controlling layer, and the other one of the pair of electrodes is exposed to the atmosphere.

In the limiting current gas sensor, when a voltage that is applied between the pair of electrodes (hereinafter, also referred to as inter-electrode applied voltage) is set to a predetermined voltage within a limiting current region, a current according to the concentration of specific components (for example, oxygen, nitrogen oxides (NOx), and the like) in the test gas flows between the pair of electrodes. This current is also termed electrode current. The limiting current gas sensor outputs a physical quantity (for example, a voltage) according to the electrode current.

For example, a limiting current gas sensor described in Japanese Patent No. 4664882 includes electrodes containing a material, such as rhodium (Rh) and platinum (Pt), having a high NOx reduction property. Such a limiting current gas sensor decomposes NOx in exhaust gas into $N_2$ and $O_2$ by applying a predetermined voltage to the electrodes, and generates an electrode current according to the amount of $O_2$. Thus, the concentration of NOx is acquired by measuring the electrode current of the limiting current gas sensor.

Fuel (such as light oil and gasoline) of an internal combustion engine mounted on a vehicle may contain a small amount of sulfur (S). When the concentration of sulfur in fuel (hereinafter, also simply referred to as sulfur concentration) is high, there is a possibility that the engine degrades or white smoke is produced. In addition, there is a possibility that sulfur poisoning of an exhaust gas control device interposed in an exhaust passage of the engine advances.

Therefore, it is desirable that the concentration of sulfur in fuel be detected and then the detected sulfur concentration be reflected in control over the engine, an alarm related to a failure of the engine be issued or the detected sulfur concentration be put to use in improvement of an on board diagnosis (OBD) on the exhaust gas control device.

Incidentally, when fuel of the engine contains sulfur (S), sulfur oxides (SOx) are contained in exhaust gas that is emitted from a combustion chamber. The concentration of SOx in exhaust gas (hereinafter, referred to as exhaust gas SOx concentration or also simply referred to as SOx concentration) increases as the concentration of sulfur in fuel increases. Thus, it is conceivable that, if the exhaust gas SOx concentration is measured, it is possible to estimate the concentration of sulfur in fuel on the basis of the measured exhaust gas SOx concentration.

SUMMARY OF THE INVENTION

A first aspect of the invention provides a control system for an internal combustion engine. The internal combustion engine includes an exhaust passage and a limiting current gas sensor. The limiting current gas sensor includes a pumping cell arranged in the exhaust passage. Exhaust gas in the exhaust passage is introduced to the pumping cell. The control system includes an electronic control unit. The electronic control unit is configured to: (i) execute step-up operation for increasing a voltage applied between a pair of electrodes of the pumping cell from a first voltage to a second voltage higher than the first voltage; (ii) execute step-down operation for, after completion of the step-up operation, reducing the applied voltage from the second voltage to a third voltage lower than the second voltage; (iii) acquire an air-fuel ratio of the exhaust gas multiple times within a first period from a start of the step-up operation to a start of the step-down operation; (iv) acquire a first waveform characteristic value indicating a characteristic of a waveform of current flowing between the pair of electrodes within a second period in which the step-down operation is executed; and (v) estimate an actual concentration of sulfur in fuel of the internal combustion engine by using the first waveform characteristic value and the plurality of acquired air-fuel ratios.

According to the above configuration, the air-fuel ratio of the engine during the step-up operation is used in estimating the concentration of sulfur in fuel. Therefore, even when the air-fuel ratio of the engine fluctuates during the step-up operation, it is possible to further accurately estimate the concentration of sulfur in fuel. Thus, it is possible to avoid a reduction in opportunity to estimate the concentration of sulfur in fuel.

In the control system, the electronic control unit may be configured to acquire a local minimum value of current flowing between the pair of electrodes within the second period, as the first waveform characteristic value.

In the control system, the electronic control unit may be configured to convert the first waveform characteristic value to a first value according to a second waveform characteristic value based on the plurality of acquired air-fuel ratios, the second waveform characteristic value is a waveform characteristic value when each of the plurality of acquired air-fuel ratios is assumed as a predetermined reference air-fuel ratio. The electronic control unit may be configured to estimate an actual concentration of sulfur in the fuel based on the first value and a first correlation, and the first correlation may be a correlation between a second value according to a third waveform characteristic value and a concentration of sulfur in the fuel, and the third waveform characteristic value is a waveform characteristic value acquired in advance when the air-fuel ratio of the exhaust gas has been continuously the reference air-fuel ratio within the first period.

According to this aspect, the acquired first waveform characteristic value is converted to the first value according to the second waveform characteristic value. The first value may be the waveform characteristic value (for example, a value having the same unit as the above-described local minimum value) itself, or may be a value (for example, the exhaust gas SOx concentration, or the like) that has a one-to-one correlation with the waveform characteristic value. An actual concentration of sulfur in fuel is estimated by applying the first value according to the second waveform characteristic value to the first correlation determined in advance and stored in the control system (a storage unit in the control system). The first correlation is a correlation obtained in advance as follows. For fuels having various concentrations of sulfur, the air-fuel ratio of the exhaust gas is kept at the reference air-fuel ratio within the first period, and the above correlation is obtained based on a second value according to a third waveform characteristic value that is obtained at this time and the concentration of sulfur in fuel that is used at this time. The second value according to the third waveform characteristic value may also be the waveform characteristic value (for example, a value having the same unit as the above-described local minimum value) itself, or may be a value (for example, the exhaust gas SOx concentration, or the like) that has a one-to-one correlation with the waveform characteristic value.

According to this aspect, for example, it is possible to estimate the concentration of sulfur in fuel without holding a map (lookup table), expressing the correlation between the waveform characteristic value or the concentration of SOx in exhaust gas and the concentration of sulfur in fuel, for each air-fuel ratio. Thus, it is possible to reduce the size of a storage area that is required for the system of the invention to hold the map.

In the control system, the electronic control unit may be configured to employ a concentration of sulfur oxide in the exhaust gas (exhaust gas SOx concentration) as the first value and the second value.

When the other condition (for example, the air-fuel ratio of the exhaust gas) remains unchanged, the concentration of sulfur oxide in the exhaust gas increases as the concentration of sulfur in the fuel increases. Thus, according to this aspect, the electronic control unit is able to acquire the concentration of sulfur oxide in exhaust gas based on current flowing between the pair of electrodes, and estimate the actual concentration of sulfur in fuel based on the concentration of sulfur oxide and the plurality of acquired air-fuel ratios.

In the control system, the electronic control unit may be configured to issue an alarm when the estimated concentration of sulfur is larger than a predetermined concentration threshold.

According to this aspect, it is possible to reliably provide information about occurrence of a state where the concentration of sulfur in fuel is high.

A second aspect of the invention provides a control system for an internal combustion engine. The internal combustion engine includes an exhaust passage and a limiting current gas sensor. The limiting current gas sensor includes a pumping cell arranged in the exhaust passage. Exhaust gas in the exhaust passage is introduced to the pumping cell. The control system includes an electronic control unit. The electronic control unit is configured to: (i) execute step-up operation for increasing a voltage applied between a pair of electrodes of the pumping cell from a first voltage to a second voltage higher than the first voltage; (ii) execute step-down operation for, after completion of the step-up operation, reducing the applied voltage from the second voltage to a third voltage lower than the second voltage; (iii) acquire a step-up air-fuel ratio based on an air-fuel ratio of the exhaust gas within a first period from a start of the step-up operation to a start of the step-down operation; (iv) acquire a local minimum value of current flowing between the pair of electrodes within a second period in which the step-down operation is executed; and (v) issue an alarm when the acquired local minimum value and the acquired step-up air-fuel ratio satisfy a predetermined condition.

With the system according to this aspect, the step-up air-fuel ratio is acquired based on the air-fuel ratio of the exhaust gas within the first period. As will be described later, the step-up air-fuel ratio may be an average of air-fuel ratios detected multiple times within the first period or may be a constant value when the air-fuel ratio is kept at the constant value within the first period.

On the other hand, as described above, the local minimum value of current flowing between the pair of electrodes within the second period has a strong correlation with the exhaust gas SOx concentration. That is, as the exhaust gas SOx concentration increases, the local minimum value decreases. On the other hand, as described above, even when the concentration of sulfur in fuel is constant, the exhaust gas SOx concentration increases as the air-fuel ratio of air-fuel mixture (that is, the air-fuel ratio of exhaust gas) within the first period decreases. Thus, when the acquired local minimum value and the acquired step-up air-fuel ratio satisfy the predetermined condition, it may be determined that the concentration of sulfur in fuel is remarkably high. For the above reason, the system of the invention according to the above aspect is allowed to provide information about the fact that the concentration of sulfur in fuel is high with a simple configuration.

In the control system, the predetermined condition may be a condition that is satisfied when the acquired local minimum value is smaller than a predetermined current threshold and the acquired step-up air-fuel ratio is larger than a predetermined air-fuel ratio threshold.

In the control system, the predetermined condition may be a condition that is satisfied when the acquired local minimum value is smaller than a current threshold that increases as the acquired step-up air-fuel ratio increases.

In the control system, the electronic control unit may be configured to acquire the air-fuel ratio of the exhaust gas multiple times within the first period, and the electronic control unit may be configured to employ an average of the plurality of acquired air-fuel ratios as the step-up air-fuel ratio.

According to this aspect, even when the air-fuel ratio is not kept constant during the step-up operation within the first period, it is possible to issue an alarm when the concentration of sulfur in fuel is high to such an extent that an alarm is required. In other words, because it is not required to keep the air-fuel ratio constant within the first period, it is possible to frequently determine whether the concentration of sulfur in fuel is high to such an extent that an alarm is required.

In the control system, the limiting current gas sensor may further include an oxygen removing unit that removes oxygen from exhaust gas that is introduced to the pumping cell. The electronic control unit may be configured to remove oxygen from exhaust gas that is introduced to the pumping cell at least within the second period with the use of the oxygen removing unit.

According to this aspect, the concentration of oxygen around the pumping cell is substantially zero within the second period. Thus, for example, it is possible to prevent the following situation. That is, a limiting current (an amount due to oxygen within current flowing between the pair of electrodes) changes because of a change in the concentration of oxygen around the pumping cell resulting from a change in the air-fuel ratio within the second period, with the result that the waveform characteristic value changes. Thus, the system according to this aspect is able to reliably estimate the concentration of sulfur in fuel even when the air-fuel ratio is not kept constant in the first or second period. In other words, it is possible to highly frequently detect the concentration of sulfur in fuel.

In the control system, the oxygen removing unit may be another pumping cell different from the pumping cell, and the electronic control unit may be configured to acquire the air-fuel ratio of the exhaust gas based on current flowing between a pair of electrodes of the oxygen removing unit. That is, a dual-cell limiting current gas sensor may be used as the limiting current gas sensor according to the aspect, the air-fuel ratio of exhaust gas may be detected by one of the pumping cells, and the waveform characteristic value may be acquired by the other one cell.

With this configuration, it is possible to also estimate the concentration of sulfur in fuel with the use of the air-fuel ratio sensor (dual-cell limiting current gas sensor) that is usually provided for the purpose of air-fuel ratio control over the engine. Thus, another sensor is not required in order to estimate the concentration of sulfur, so it is possible to reduce the cost of the system.

In the control system, the electronic control unit may be configured to control the internal combustion engine such that the air-fuel ratio of the exhaust gas is kept constant within the second period.

According to this aspect as well, it is possible to suppress a change in the waveform characteristic value due to a change in the concentration of oxygen around the pumping cell within the second period. This aspect is particularly effective in the case where the above-described limiting current gas sensor does not include the above-described oxygen removing unit; however, this aspect is also applicable even in the case where the above-described limiting current gas sensor includes the above-described oxygen removing unit. This is because there is a case where the oxygen removing unit cannot completely remove oxygen.

The invention is also applicable to a vehicle on which the control system for an internal combustion engine is mounted.

A third aspect of the invention provides a control method for an internal combustion engine. The internal combustion engine includes an exhaust passage and a limiting current gas sensor. The limiting current gas sensor includes a pumping cell arranged in the exhaust passage. Exhaust gas in the exhaust passage is introduced to the pumping cell. The control method includes: (i) executing step-up operation for increasing a voltage applied between a pair of electrodes of the pumping cell from a first voltage to a second voltage higher than the first voltage; (ii) executing step-down operation for, after completion of the step-up operation, reducing the applied voltage from the second voltage to a third voltage lower than the second voltage; (iii) acquiring an air-fuel ratio of the exhaust gas multiple times within a first period from a start of the step-up operation to a start of the step-down operation; (iv) acquiring a first waveform characteristic value indicating a characteristic of a waveform of current flowing between the pair of electrodes within a second period in which the step-down operation is executed; and (v) estimating an actual concentration of sulfur in fuel of the internal combustion engine by using the first waveform characteristic value and the plurality of acquired air-fuel ratios.

A fourth aspect of the invention provides a control system for an internal combustion engine. The internal combustion engine includes an exhaust passage and a limiting current gas sensor. The limiting current gas sensor includes a pumping cell arranged in the exhaust passage. Exhaust gas in the exhaust passage is introduced to the pumping cell. The control method includes: (i) executing step-up operation for increasing a voltage applied between a pair of electrodes of the pumping cell from a first voltage to a second voltage higher than the first voltage; (ii) executing step-down operation for, after completion of the step-up operation, reducing the applied voltage from the second voltage to a third voltage lower than the second voltage; (iii) acquiring a step-up air-fuel ratio based on an air-fuel ratio of the exhaust gas within a first period from a start of the step-up operation to a start of the step-down operation; (iv) acquiring a local minimum value of current flowing between the pair of electrodes within a second period in which the step-down operation is executed; and (v) issuing an alarm when the acquired local minimum value and the acquired step-up air-fuel ratio satisfy a predetermined condition.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIG. 22 is a time chart that shows temporal changes in applied voltage, electrode current and air-fuel ratio at the time when the fourth control system according to the fourth embodiment has executed step-up operation and step-down operation.

DETAILED DESCRIPTION OF EMBODIMENTS

Figure 1:
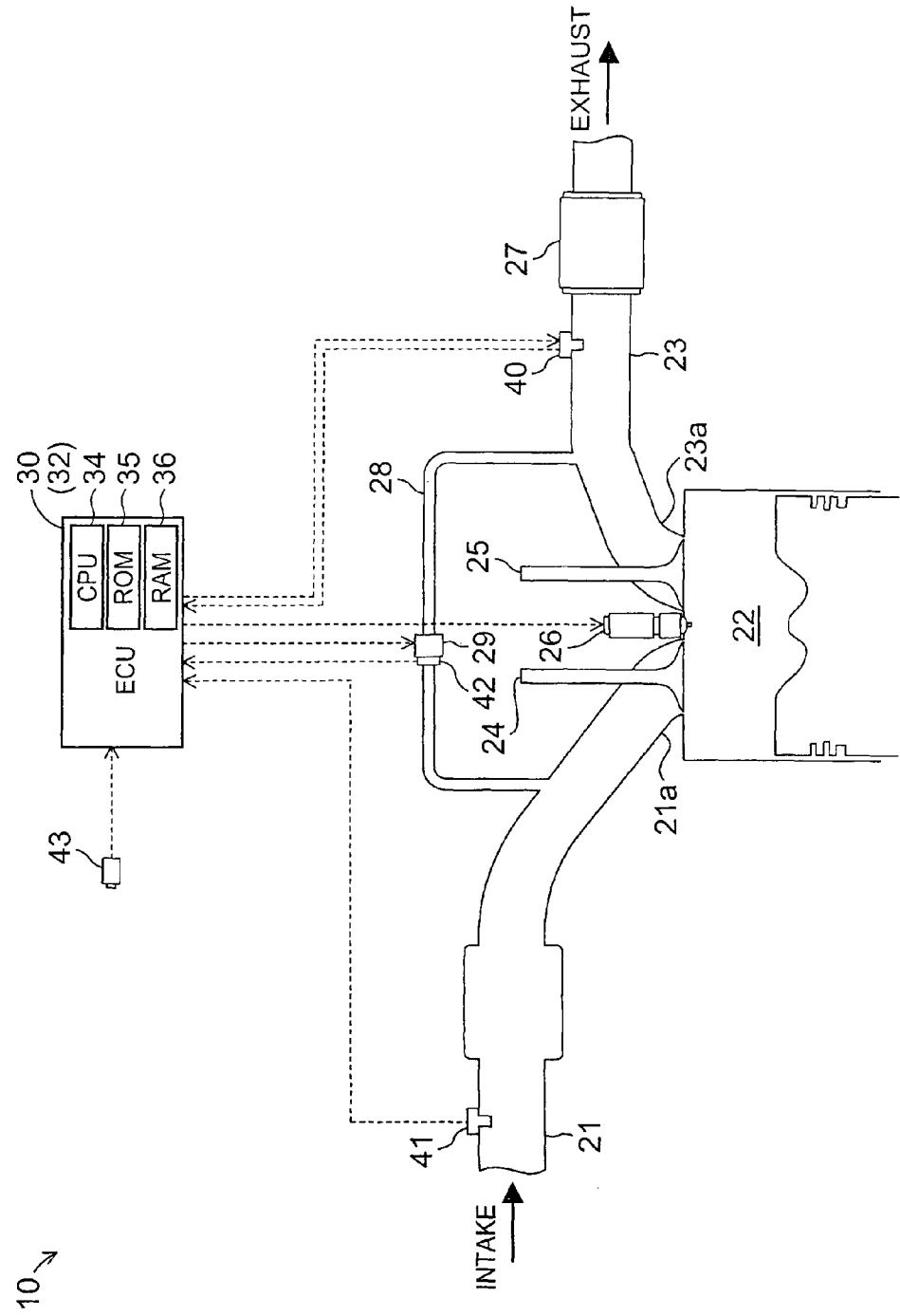
FIG. 1 is a schematic configuration view (cross-sectional view) of an internal combustion engine to which a control system (first control system) according to a first embodiment of the invention is applied.

The inventors have been studying a technique for measuring an exhaust gas SOx concentration with the use of a limiting current gas sensor and then estimating a concentration of sulfur in fuel on the basis of the measured exhaust gas SOx concentration.

As a result, the inventors found that, when step-up operation is executed for increasing a voltage (inter-electrode applied voltage) that is applied between a pair of electrodes from a predetermined first voltage to a second voltage and, after completion of the step-up operation, step-down operation is executed for reducing the inter-electrode applied voltage from the second voltage to a third voltage, current flowing between the pair of electrodes (electrode current) within a period during which the step-down operation is executed exhibits a change according to the exhaust gas SOx concentration. The pair of electrodes constitute a pumping cell included in the limiting current gas sensor. The third voltage may be any voltage as long as the electrode current exhibits a change according to the exhaust gas SOx concentration. That is, the third voltage may be equal to the first voltage or may be different from the first voltage.

More specifically, when the above-described step-up operation is executed in the case where fuel containing a sulfur (S) component is used in an internal combustion engine, sulfur (S) is produced as a result of decomposition (reduction) of sulfur oxides (SOx) contained in exhaust gas, and the sulfur (S) is adsorbed to one of the electrodes (cathode). The amount of sulfur (S) that is adsorbed to the one of the electrodes (cathode) changes with the exhaust gas SOx concentration. Subsequently, when the above-described step-down operation is executed, sulfur (S) adsorbed to the one of the electrodes (cathode) is reoxidized into sulfur oxides (SOx) again. The inventors found that the waveform of electrode current that changes because of the reoxidation of sulfur (S) has a strong correlation with the exhaust gas SOx concentration.

Thus, the inventors reached such an idea that, when a value that indicates a characteristic of the waveform of electrode current (hereinafter, also simply referred to as "waveform characteristic value") is acquired within a period in which the step-down operation is executed, it is possible to estimate an actual concentration of sulfur in fuel on the basis of the acquired waveform characteristic value.

However, even when the concentration of sulfur in fuel is constant, the exhaust gas SOx concentration changes with the air-fuel ratio of air-fuel mixture that is supplied to the engine (hereinafter, also simply referred to as the air-fuel ratio of the engine). More specifically, the exhaust gas SOx concentration decreases as the air-fuel ratio of the engine increases. Thus, to estimate the concentration of sulfur in fuel, it is required not only to measure the exhaust gas SOx concentration but also to identify the air-fuel ratio of the engine at the time when the exhaust gas SOx concentration is measured.

From the above viewpoint, a method of keeping the air-fuel ratio of the engine at a constant value in a period in which at least step-up operation is executed (that is, a period for producing sulfur (S) by reducing sulfur oxides (SOx) in exhaust gas and then adsorbing the sulfur (S) to one of the electrodes (cathode)) is conceivable. However, the air-fuel ratio of the engine is, for example, changed in order to satisfy driver's required torque or changes with an operating state of the engine. Thus, there are many cases where it is actually difficult to keep the air-fuel ratio of the engine at a constant value over a certain period. As a result, an opportunity to carry out a method of detecting the exhaust gas SOx concentration is limited in the case where the air-fuel ratio of the engine is constant, with the result of a reduction in opportunity to estimate the concentration of sulfur in fuel.

In light of the above point, an electronic control unit included in a control system for an internal combustion engine according to the invention (hereinafter, referred to as the system of the invention) executes the step-up operation and the step-down operation, and acquires the air-fuel ratio of the exhaust gas multiple times within a first period from a start of the step-up operation to a start of the step-down operation. The electronic control unit acquires a waveform characteristic value (first waveform characteristic value) that indicates a characteristic of the waveform of current flowing between the pair of electrodes within a second period in which the step-down operation is executed. The electronic control unit estimates an actual concentration of sulfur in fuel of the internal combustion engine by using the acquired waveform characteristic value and the plurality of acquired air-fuel ratios. The system of the invention may once convert the acquired waveform characteristic value to the exhaust gas SOx concentration and then may estimate an actual concentration of sulfur in the fuel from the exhaust gas SOx concentration and the plurality of acquired air-fuel ratios. The system of the invention may estimate an actual concentration of sulfur in the fuel from the acquired waveform characteristic value and the plurality of acquired air-fuel ratios without converting the waveform characteristic value to the exhaust gas SOx concentration.

Figure 3:
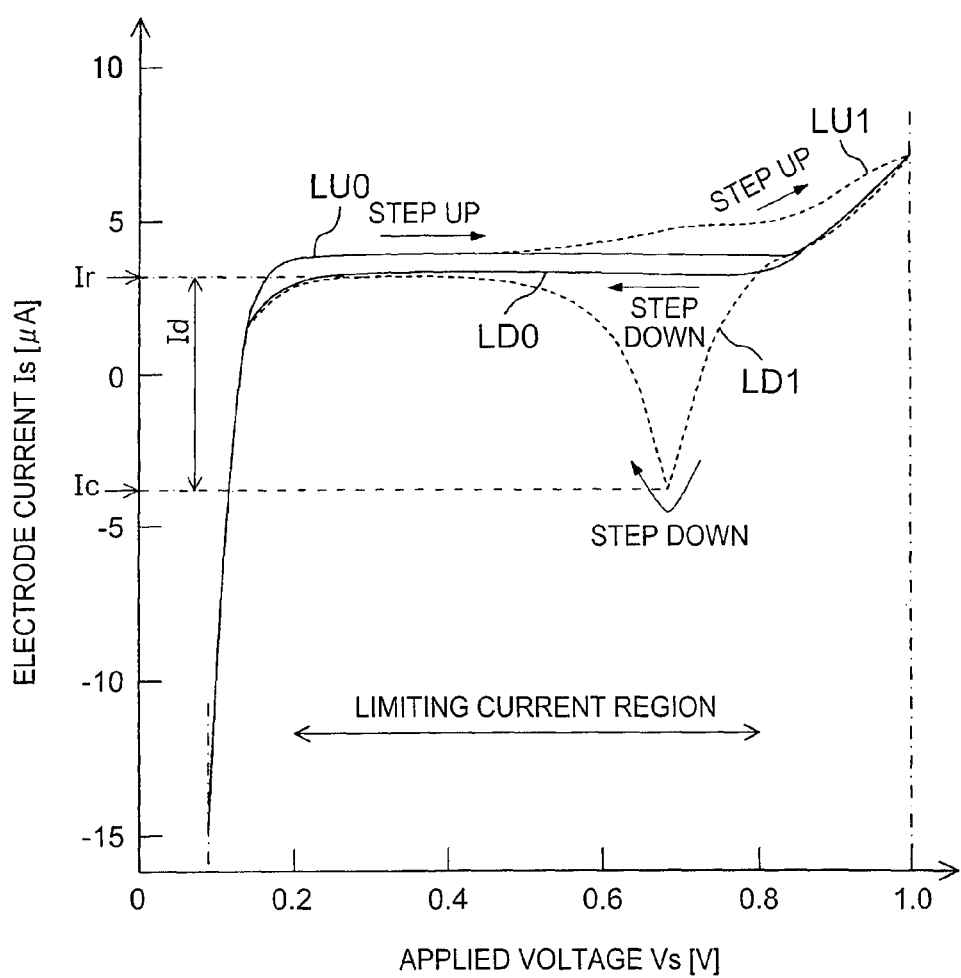
FIG. 3 is a graph that shows the correlation between an applied voltage and electrode current of the limiting current gas sensor.
Figure 4:
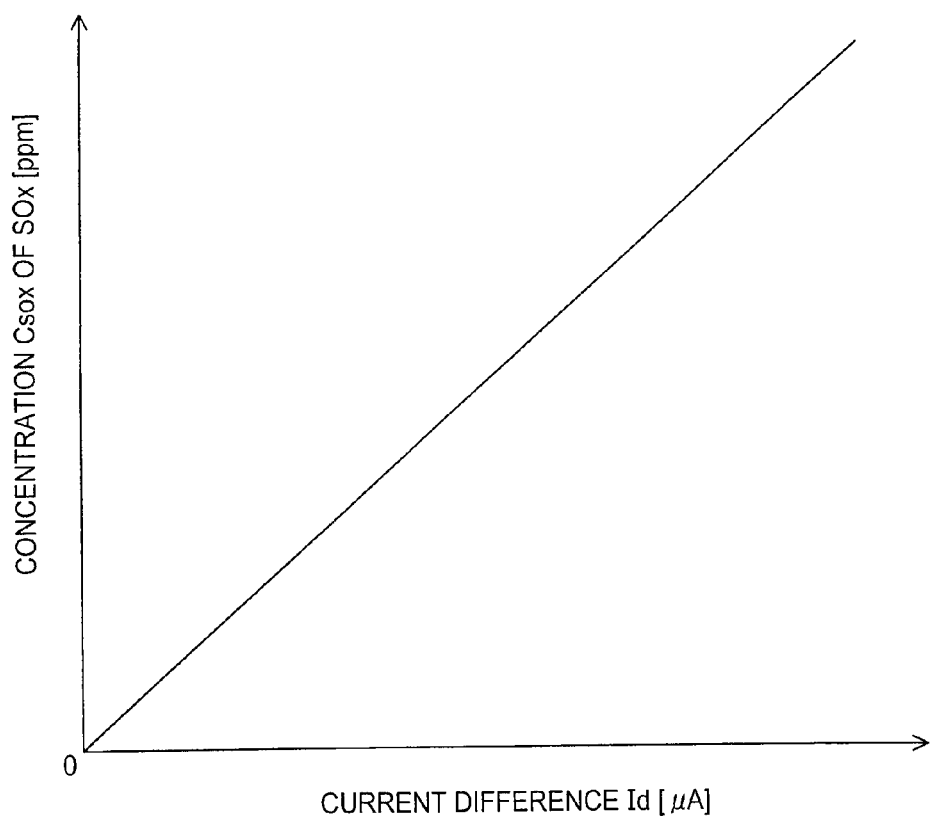
FIG. 4 is a graph that shows the correlation between a current difference and a concentration of SOx in exhaust gas.

The inventors found that a current value at the time when current flowing between the pair of electrodes shifts from a decrease to an increase within the second period (that is, a local minimum value) may be employed as one example of the waveform characteristic value. That is, as shown in FIG. 3 and FIG. 4, because a local minimum value (Ic) within the second period has a strong correlation with the exhaust gas SOx concentration, the local minimum value (Ic) within the second period also has a strong correlation with the concentration of sulfur in fuel. Thus, according to the above aspect, it is possible to easily acquire the waveform characteristic value.

FIG. 3 and FIG. 4 show that, instead of the local minimum value (Ic), a current difference Id between a limiting current Ir at completion of the step-down operation and a local minimum value Ic (Id=Ir−Ic) has a strong correlation with the exhaust gas SOx concentration. However, the limiting current Ir at completion of the step-down operation is substantially constant irrespective of the air-fuel ratio during the step-down operation in the case where a dual-cell limiting current sensor (described later) is used, so FIG. 3 and FIG. 4 show that the local minimum value (Ic) within the second period has a strong correlation with the exhaust gas SOx concentration. In contrast, in the case where a single-cell limiting current sensor (described later) is used, the limiting current Ir at completion of the step-down operation changes depending on the air-fuel ratio during the step-down operation; however, when the air-fuel ratio is kept at a specific constant air-fuel ratio during the step-down operation, the limiting current Ir is a predetermined constant value, so FIG. 3 and FIG. 4 still show that the local minimum value (Ic) within the second period has a strong correlation with the exhaust gas SOx concentration.

Not only the above-described local minimum value Ic but also the above-described current difference Id (Id=Ir−Ic; the height of a peak), an accumulated value of a deviation from the limiting current Ir of electrode current, or the like, may be employed as the waveform characteristic value.

Hereinafter, a control system (hereinafter, also referred to as first control system) for an internal combustion engine according to a first embodiment of the invention will be described with reference to the accompanying drawings. The first control system is applied to an engine 10 of which the schematic configuration is shown in FIG. 1. The engine 10 is a diesel engine. The engine 10 includes an intake passage 21, a combustion chamber 22, an exhaust passage 23, an intake valve 24, an exhaust valve 25, a fuel injection valve 26, an exhaust gas control device 27, an exhaust gas recirculation pipe 28 and an EGR control valve 29. The intake passage 21 includes an intake port 21a. The exhaust passage 23 includes an exhaust port 23a.

The intake valve 24 is arranged at a cylinder head portion. The intake valve 24 opens or closes a communicating portion between the intake port 21a and the combustion chamber 22 by being driven by an intake camshaft (not shown). The exhaust valve 25 is arranged at the cylinder head portion. The exhaust valve 25 opens or closes a communicating portion between the exhaust port 23a and the combustion chamber 22 by being driven by an exhaust camshaft (not shown).

The fuel injection valve 26 is arranged at the cylinder head portion so as to be able to inject fuel into the combustion chamber 22. The fuel injection valve 26 directly injects fuel into the combustion chamber 22 in response to a command of an ECU 30 (described later).

The exhaust gas control device (an exhaust gas purification catalyst, a DPF, and the like) 27 is interposed in the exhaust passage 23. The exhaust gas control device 27 purifies NOx, and the like, in exhaust gas, and traps particulate matter.

The exhaust gas recirculation pipe 28 and the EGR control valve 29 constitute an EGR device. The exhaust gas recirculation pipe 28 returns part of exhaust gas, flowing through the exhaust passage 23, to the intake passage 21 as EGR gas. The EGR control valve 29 controls the amount of EGR gas flowing through the exhaust gas recirculation pipe 28 in response to a command of the ECU 30.

The electronic control unit (ECU) 30 includes a CPU 34, a ROM 35 and a RAM 36. The ROM 35 stores programs, maps, and the like, that are executed by the CPU 34. The RAM 36 temporarily stores data. The ECU 30 is connected to sensors described below.

A gas sensor 40 is a dual-cell limiting current sensor. The gas sensor 40 is arranged on the upstream side of the exhaust gas control device 27. The structure and operation of the gas sensor 40 will be described in detail later. An air flow meter 41 measures the mass flow rate (intake air amount) of intake air (fresh air that does not contain EGR gas) that passes through the intake passage 21, and generates a signal that indicates the intake air amount Ga. An EGR control valve opening degree sensor 42 generates a signal that indicates an EGR valve open rate (opening degree) Er of the EGR control valve 29. A crank angle sensor 43 generates a signal according to a rotation position of a crankshaft (not shown) of the engine 10. The ECU 30 calculates an engine rotation speed NE of the engine 10 on the basis of a signal from the crank angle sensor 43.

Figure 2:
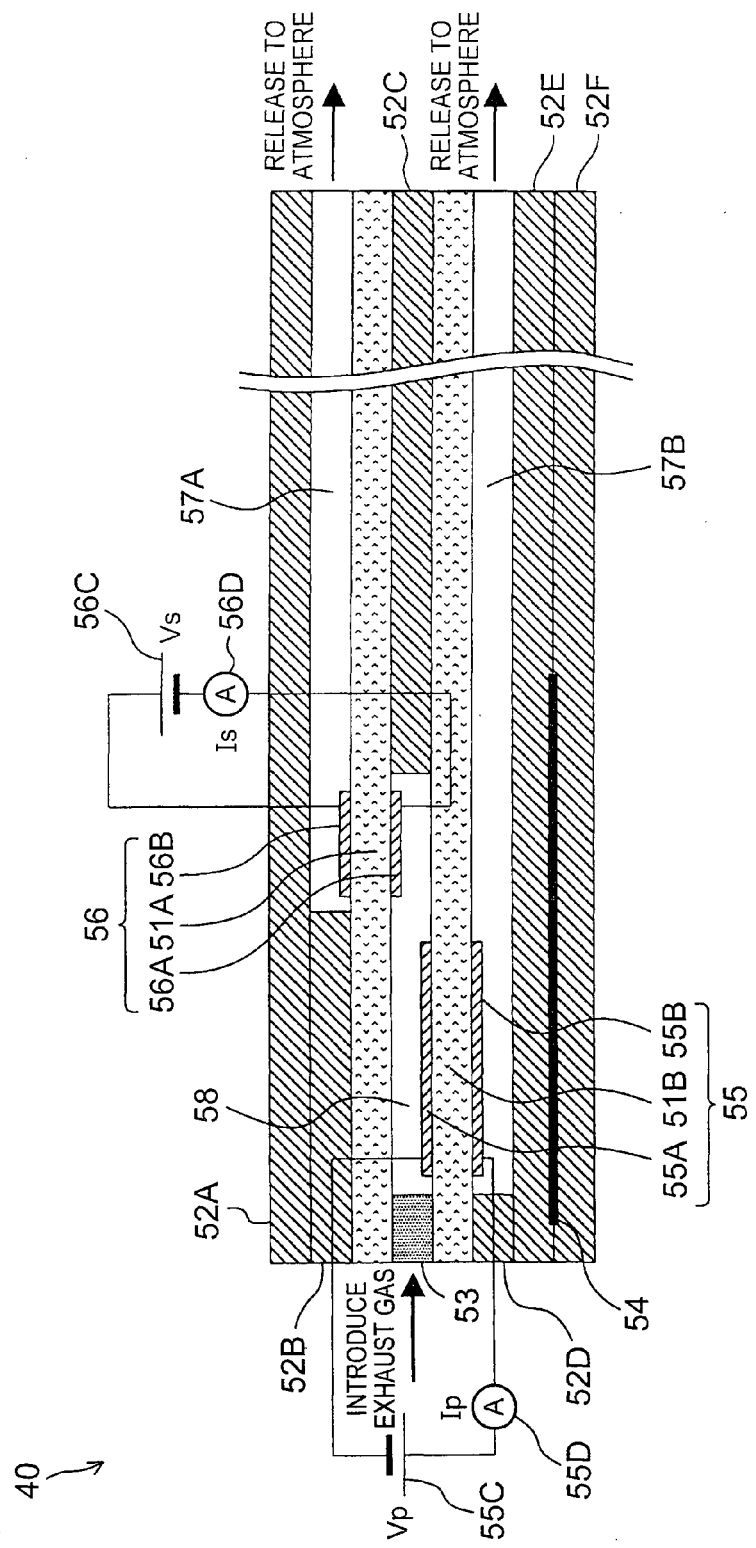
FIG. 2 is a schematic configuration view of a dual-cell limiting current gas sensor included in the internal combustion engine to which the first control system according to the first embodiment is applied.

As shown in FIG. 2, the gas sensor 40 includes a first solid electrolyte layer 51A, a second solid electrolyte layer 51B, a first alumina layer 52A, a second alumina layer 52B, a third alumina layer 52C, a fourth alumina layer 52D, a fifth alumina layer 52E, a sixth alumina layer 52F, a diffusion-controlling layer (diffusion resistance layer) 53 and a heater 54.

Each of the first solid electrolyte layer 51A and the second solid electrolyte layer 51B includes zirconia, or the like, and has an oxide ion conductivity. The first to sixth alumina layers 52A to 52F are dense (gas impermeable) layers containing alumina. The diffusion-controlling layer 63 is a porous layer, and is a gas permeable layer. The heater 54 is a heating element that is heated through energization.

The layers of the gas sensor 40 are laminated in order of the sixth alumina layer 52F, the fifth alumina layer 52E, the fourth alumina layer 52D, the second solid electrolyte layer 51B, the diffusion-controlling layer 53 and third alumina layer 52C, the first solid electrolyte layer 51A, the second alumina layer 52B, and the first alumina layer 52A from the lower side.

A first atmosphere introduction passage 57A is a space defined by the first alumina layer 52A, the second alumina layer 52B and the first solid electrolyte layer 51A, and directly communicates with the atmosphere outside. A second atmosphere introduction passage 57B is a space defined by the second solid electrolyte layer 51B, the fourth alumina layer 52D and the fifth alumina layer 52E, and directly communicates with the atmosphere outside.

An internal space 58 is a space defined by the first solid electrolyte layer 51A, the second solid electrolyte layer 51B, the diffusion-controlling layer 53 and the third alumina layer 52C, and communicates with the inside of the exhaust passage 23 via the diffusion-controlling layer 53. Thus, when the pressure in the exhaust passage 23 is higher than the pressure in the internal space 58 by a predetermined value or larger, exhaust gas in the exhaust passage 23 is introduced into the internal space 58 at a constant rate irrespective of the pressure in the exhaust passage 23. That is, the diffusion-controlling layer 53 is able to introduce exhaust gas in the exhaust passage 23 into the gas sensor 40 (internal space 58) while controlling the rate of exhaust gas. The heater 54 is arranged between the fifth alumina layer 52E and the sixth alumina layer 52F.

A first cell cathode electrode 55A and a first cell anode electrode 55B are electrodes containing a platinum-group element, such as platinum and rhodium, or an alloy of the platinum-group element. The first cell cathode electrode 55A is a cathode-side electrode. The first cell anode electrode 55B is an anode-side electrode.

The first cell cathode electrode 55A is fixed to one-side surface of the second solid electrolyte layer 51B (specifically, the surface of the second solid electrolyte layer 51B, which defines the internal space 58). The first cell anode electrode 55B is fixed to the other-side surface of the second solid electrolyte layer 51B (specifically, the surface of the second solid electrolyte layer 51B, which defines the second atmosphere introduction passage 57B). The first cell cathode electrode 55A, the first cell anode electrode 55B and the second solid electrolyte layer 51B constitute a first cell 55.

A first cell power supply 55C is able to apply an applied voltage Vp to the first cell cathode electrode 55A and the first cell anode electrode 55B. The applied voltage Vp is controlled by the ECU 30. An ammeter 55D generates a signal (voltage) that indicates an electrode current Ip flowing through the first cell 55, and supplies the signal to the ECU 30.

A second cell cathode electrode 56A and a second cell anode electrode 56B are electrodes containing a platinum-group element, such as platinum and rhodium, or an alloy of the platinum-group element. The second cell cathode electrode 56A is a cathode-side electrode. The second cell anode electrode 56B is an anode-side electrode.

The second cell cathode electrode 56A is fixed to one-side surface of the first solid electrolyte layer 51A (specifically, the surface of the first solid electrolyte layer 51A, which defines the internal space 58). The second cell anode electrode 56B is fixed to the other-side surface of the first solid electrolyte layer 51A (specifically, the surface of the first solid electrolyte layer 51A, which defines the first atmosphere introduction passage 57A). The second cell cathode electrode 56A, the second cell anode electrode 56B and the first solid electrolyte layer 51A constitute a second cell 56. The second cell 56 is also referred to as pumping cell or sensor cell.

A second cell power supply 56C is able to apply an applied voltage (inter-electrode applied voltage) Vs to the second cell cathode electrode 56A and the second cell anode electrode 56B. The applied voltage Vs is controlled by the ECU 30. The ammeter 56D generates a signal (voltage) that indicates an electrode current Is flowing through the second cell 56, and supplies the signal to the ECU 30.

Next, a method of detecting the exhaust gas SOx concentration and a method of estimating the concentration of sulfur in fuel will be described while the operation of the gas sensor 40 is described.

Initially, the operation of the first cell will be described. When the applied voltage Vp is applied by the first cell power supply 55C between the first cell cathode electrode 55A and the first cell anode electrode 55B, oxygen contained in exhaust gas in the internal space 58 becomes oxygen ions at the first cell cathode electrode 55A. The oxygen ions migrate through the second solid electrolyte layer 51B to the first cell anode electrode 55B, and become oxygen at the first cell anode electrode 55B. The oxygen is released into the atmosphere through the second atmosphere introduction passage 57B. A phenomenon that oxygen migrates from the internal space 58 to the second atmosphere introduction passage 57B is also referred to as pumping. As a result of migration of oxygen ions, the electrode current Ip flows through the first cell 55 (that is, between the first cell cathode electrode 55A and the first cell anode electrode 55B).

Because the amount of oxygen that is pumped (that migrates) from the internal space 58 to the second atmosphere introduction passage 57B as the applied voltage Vp increases, the electrode current Ip increases. However, as described above, because the amount of exhaust gas that is introduced into the internal space 58 by the diffusion-controlling layer 53 is limited to a constant rate, the amount of oxygen in the internal space 58 is also limited. Therefore, as the amount of oxygen in the internal space 58 approaches zero as a result of pumping, there can occur a phenomenon that the electrode current Ip does not increase any more even when the applied voltage Vp increases. The range of the applied voltage Vp in which the phenomenon occurs is also referred to as limiting current region (oxygen limiting current region). The electrode current Ip at the time when the phenomenon is occurring is a limiting current Ig.

Thus, the limiting current Ig has a correlation with the air-fuel ratio AF of exhaust gas. Thus, the first cell 55 removes oxygen in the internal space 58 through pumping, and also operates as an air-fuel ratio sensor that detects the air-fuel ratio AF (see, for example, Japanese Patent Application Publication No. 2000-65782 (JP 2000-65782 A) and Japanese Patent Application Publication No. 2004-69547 (JP 2004-69547 A) for a method of detecting the air-fuel ratio on the basis of the limiting current Ig).

Next, the operation of the second cell will be described. When the applied voltage Vs that is applied by the second cell power supply 56C between the second cell cathode electrode 56A and the second cell anode electrode 56B is increased, SOx and remaining oxygen not pumped by the first cell in the internal space 58 are reduced, and oxygen ions generated as a result of the reduction migrate to the second cell anode electrode 56B through the first solid electrolyte layer 51A. As a result, the electrode current Is flows through the second cell 56 (that is, between the second cell cathode electrode 56A and the second cell anode electrode 56B). After that, when the applied voltage Vs is reduced, sulfur (S) adhered to the second cell cathode electrode 56A is reoxidized, with the result that the electrode current Is flows. Hereinafter, this point will be described in more detail.

The electrode current Is changes as shown in FIG. 3 as the applied voltage Vs is changed. In FIG. 3, the continuous line LU0 and the continuous line LD0 indicate the electrode current Is in the case where exhaust gas in the exhaust passage 23 does not contain SOx. The continuous line LU0 indicates the electrode current Is at the time when the applied voltage Vs is gradually increased from 0.1 V to 1.0 V. The continuous line LD0 indicates the electrode current Is at the time when the applied voltage Vs is gradually reduced from 1.0 V to 0.1 V after the applied voltage Vs is increased.

As indicated by the continuous line LU0, in the case where exhaust gas does not contain SOx, within the limiting current region (in this example, in the region in which the applied voltage Vs is between 0.2 V and 0.8 V), the amount of remaining oxygen not pumped by the first cell 55 is slight and a constant amount, so the electrode current Is is substantially constant even when the applied voltage Vs increases. After that, when the applied voltage Vs further increases toward 1.0 V, molecules containing an oxygen atom, other than $O_2$ or SOx, contained in exhaust gas (for example, water ($H_2O$), carbon dioxide ($CO_2$), and the like; and hereinafter, also referred to as oxygen atom containing molecules) are decomposed, and current due to pumping of the resultant oxygen flows through the first solid electrolyte layer 51A. When the applied voltage Vs falls within the range from 0.8 V to 1.0 V, not all the oxygen atom containing molecules are reduced, so the electrode current Is increases with an increase in the applied voltage Vs.

Subsequently, the electrode current Is is reduced from 1.0 V. At this time, as indicated by the continuous line LD0, the electrode current Is decreases with a decrease in the applied voltage Vs because of the same reason as the above description until the applied voltage Vs reaches 0.8 V. When the applied voltage Vs is further reduced from 0.8 V toward 0.2 V, the oxygen atom containing molecules are not decomposed, and the amount of remaining oxygen not pumped by the first cell is slight and a constant amount, so the electrode current Is is substantially constant even when the applied voltage Vs decreases.

As indicated by the dashed line LU1, even in the case where exhaust gas contains SOx, but when the applied voltage Vs is being increased from 0.2 V to about 0.5 V, SOx is not reduced because the applied voltage Vs is low. Thus, as well as the continuous line LU0, the electrode current Is becomes substantially constant. When the applied voltage Vs becomes higher than a value close to 0.5 V, SOx is reduced, and current due to pumping of resultant oxygen flows through the first solid electrolyte layer 51A. However, when the applied voltage Vs falls within the range from 0.5 V to 1.0 V, not all the SOx is reduced, so the electrode current Is increases with an increase in the applied voltage Vs. When the applied voltage Vs falls within the range from 0.8 V to 1.0 V, current due to reduction of the oxygen atom containing molecules is superimposed on current due to reduction of SOx. Sulfur (S) produced as a result of reduction of SOx is accumulated (adsorbed) on the first cell cathode electrode 55A.

When the applied voltage Vs is reduced from 1.0 V, the electrode current Is steeply decreases, becomes a local minimum value Ic and then shifts into an increase, as indicated by the dashed line LD1. Such a change in the electrode current Is is conceivably due to the fact that sulfur (S) produced at the time when the applied voltage Vs is increased to 1.0 V and accumulated on the first cell cathode electrode 55A is reoxidized and returns into sulfur oxides (SOx). Although the reason of occurrence of the phenomenon (phenomenon that the electrode current Is decreases, becomes the local minimum value Ic and then shifts into an increase) is not apparent at this point in time, it is estimated that there occurs a phenomenon similar to a known phenomenon that the peak of response current arises near an oxidation-reduction potential in a general method of measuring the electrochemical property of a physical object (that is, cyclic voltammetry).

In addition, when the applied voltage Vs is reduced from a value near 0.4 V to a value near 0.25 V, the electrode current Is becomes the substantially constant limiting current Ir. This is presumably because reoxidation of sulfur (S) accumulated on the first cell cathode electrode 55A substantially completes. After that, when the applied voltage Vs is reduced from a value near 0.25 V to 0.1 V, the electrode current Is further decreases from the limiting current Ir.

Next, the method of detecting the exhaust gas SOx concentration will be described. The inventors obtained the finding that, because the waveform indicated by the dashed line LD1 (the waveform of the electrode current Is at the time when the applied voltage Vs is reduced) changes with an actual exhaust gas SOx concentration, it is possible to detect or acquire the exhaust gas SOx concentration Csox by utilizing a value indicating the characteristic of the waveform of the electrode current Is at that time (waveform characteristic value).

This finding is obtained through an experiment, and its grounds are estimated as follows although they are not always clear. That is, as described above, when the applied voltage Vs is increased from the voltage (0.2 V) at which reduction of SOx does not occur to a voltage (for example, a voltage of 0.8 V to 1.0 V) higher than the voltage at which reduction of SOx occurs, sulfur (S) produced as a result of reduction of SOx is accumulated (adsorbed) on the first cell cathode electrode 55A. At this time, the amount of sulfur (S) that is accumulated (adsorbed) on the first cell cathode electrode 55A increases as the exhaust gas SOx concentration increases. Therefore, as the exhaust gas SOx concentration increases, the amount of sulfur (S) that is rapidly reoxidized per unit time at the time when the applied voltage Vs is reduced from a voltage higher than the voltage at which reduction of SOx occurs to the voltage at which reduction of SOx does not occur (during step-down operation) increases. Thus, the waveform of the electrode current Is during step-down operation becomes a waveform having a deeper peak (that is, a waveform having a smaller local minimum value Ic) as the exhaust gas SOx concentration increases.

The method of detecting the exhaust gas SOx concentration will be more specifically described. The inventors investigated the correlation between a current difference Id and an exhaust gas SOx concentration Csox by using the current difference Id (that is, Id=Ir−Ic) between the limiting current Ir and the local minimum value Ic in the dashed line LD1 as one waveform characteristic value. As a result, as shown in FIG. 4, it has been confirmed that there is a strong correlation between the current difference Id and the exhaust gas SOx concentration Csox. Thus, the first control system acquires in advance the correlation between a current difference Id and an exhaust gas SOx concentration Csox and stores the correlation in the ROM 35 in map form, and then detects an actual exhaust gas SOx concentration Csox by applying an actual current difference Id obtained during step-down operation to the correlation.

In principle, the second cell 56 can reduce not only SOx but also oxygen in the internal space 58, so the electrode current Is increases with the amount of oxygen reduced. However, because the concentration of oxygen in the internal space 58 approaches zero as a result of pumping by the first cell 55, the influence of reduction of oxygen on the electrode current Is is excluded. As a result, the second cell 56 (that is, the limiting current gas sensor 40) is able to accurately detect the concentration of SOx.

Next, the method of estimating the concentration Cs of sulfur in fuel will be described. Even when the concentration Cs of sulfur is constant, but when the air-fuel ratio of combusting air-fuel mixture changes, the concentration Csox of SOx in exhaust gas also changes. The air-fuel ratio of combusting air-fuel mixture and the air-fuel ratio AF of exhaust gas are substantially the same value. Thus, by using the air-fuel ratio AF of exhaust gas and the concentration of SOx in exhaust gas, it is possible to estimate the concentration Cs of sulfur.

Figure 5:
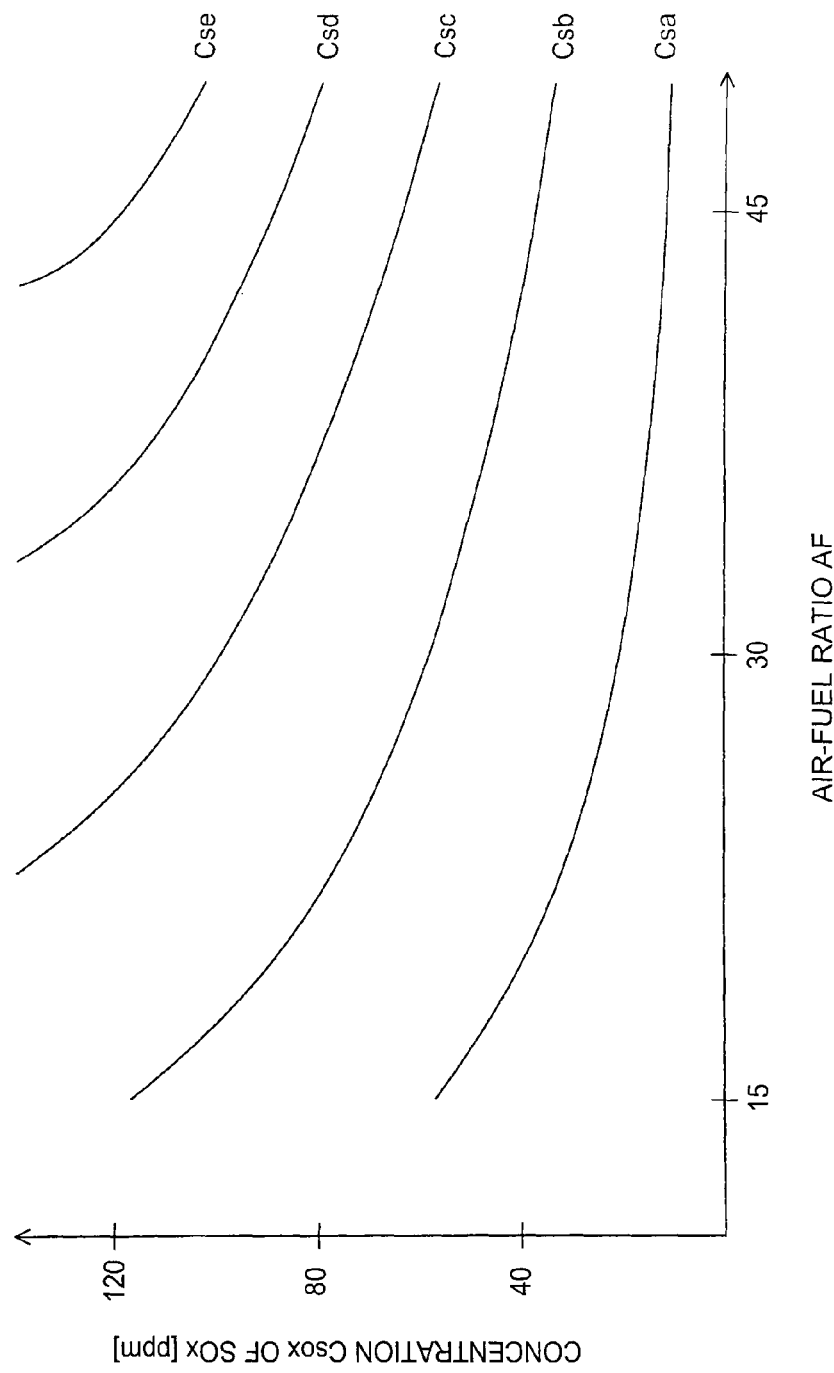
FIG. 5 is a graph that shows the correlation between an air-fuel ratio and a concentration of SOx in exhaust gas for each concentration of sulfur in fuel.

Specifically, the correlation among the air-fuel ratio AF, the concentration Csox of SOx in exhaust gas and the concentration Cs of sulfur is as shown in FIG. 5. FIG. 5 shows the correlation between the air-fuel ratio AF and the exhaust gas SOx concentration for each concentration Cs of sulfur (Csa<Csb<Csc<Csd<Cse).

As described with reference to FIG. 4, there is a one-to-one correlation between the concentration Csox of SOx in exhaust gas and the waveform characteristic value (current difference Id), so it is also possible to estimate the concentration Cs of sulfur by using the air-fuel ratio AF of exhaust gas and the waveform characteristic value.

However, as described above, in order to detect the exhaust gas SOx concentration Csox with the use of the gas sensor 40, it is required to accumulate sulfur (S) by reducing SOx on the first cell cathode electrode 55A through an increase in the applied voltage Vs over a predetermined time, and, after that, reoxidize the sulfur (S) into SOx by reducing the applied voltage Vs over a predetermined time. That is, a certain time is required to detect the exhaust gas SOx concentration Csox.

On the other hand, the air-fuel ratio of the engine generally momentarily changes with a required torque and an engine operating state (intake air amount Ga, rotation speed NE, and the like). Thus, usually, the air-fuel ratio AF also changes while the applied voltage Vs is being increased, so the actual exhaust gas SOx concentration changes. Therefore, in order to estimate the concentration of sulfur in fuel by using the correlation shown in FIG. 5, it is required to keep the air-fuel ratio AF during an increase in the applied voltage Vs at a constant value irrespective of the required torque, the engine operating state, or the like.

However, the air-fuel ratio of the engine is, for example, changed in order to satisfy the driver's required torque or changes with the operating state of the engine. Thus, in most cases, it is actually difficult to constantly keep the air-fuel ratio of the engine over a certain period. As a result, an opportunity to carry out the method of keeping the air-fuel ratio AF during an increase in the applied voltage Vs at a constant value is limited, with the result of a reduction in opportunity to estimate the concentration of sulfur in fuel.

Therefore, the first control system acquires the air-fuel ratio AF during an increase in the applied voltage Vs each time a lapse of a predetermined time instead of keeping the air-fuel ratio AF during an increase in the applied voltage Vs at a constant value. In addition, the first control system executes a correction process for correcting the exhaust gas SOx concentration Csox (or a first waveform characteristic value) obtained as described above by using the plurality of acquired air-fuel ratios AF, and then estimates the concentration of sulfur in fuel. Hereinafter, the correction process will be described.

Figure 6:
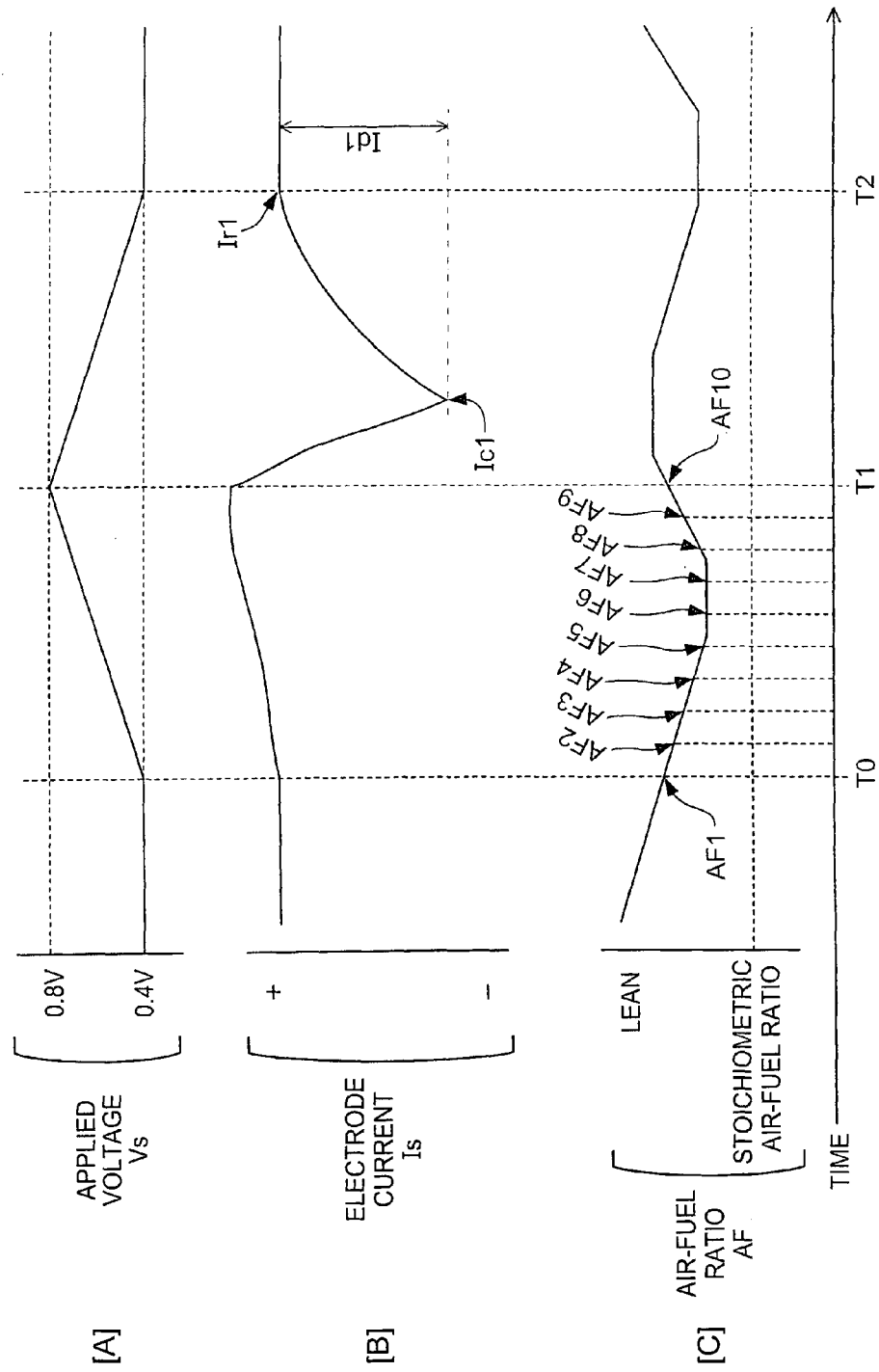
FIG. 6 is a time chart that shows temporal changes in applied voltage, electrode current and air-fuel ratio at the time when the first control system according to the first embodiment has executed step-up operation and step-down operation.

When the concentration Csox of SOx is not detected (that is, in a period before time T0 in FIG. 6), the ECU 30 of the first control system keeps the applied voltage Vs, which is applied to the gas sensor 40 (second cell 56), at a first voltage Vs1 (in this example, 0.4 V). The first voltage Vs1 is a voltage within the above-described limiting current region (region in which pumping of oxygen has reached a limit) and is a voltage lower than a voltage at which reduction of SOx occurs.

At timing (time T0 in FIG. 6) at which the concentration Csox of SOx should be detected, the ECU 30 increases the applied voltage Vs from the first voltage Vs1 (in this example, 0.4 V) to a second voltage Vs2 (in this example, 0.8 V) over a predetermined time. As a result, the applied voltage Vs reaches the second voltage Vs2 at time T1. Operation for increasing the applied voltage Vs, which is executed by the ECU 30 when the ECU 30 detects the concentration Csox of SOx, is also referred to as step-up operation. The second voltage Vs2 is a voltage higher than a voltage at which reduction (decomposition) of SOx occurs. In addition, the second voltage Vs2 is desirably a voltage lower than a voltage at which the above-described oxygen atom containing molecules are reduced (decomposed).

Figure 7:
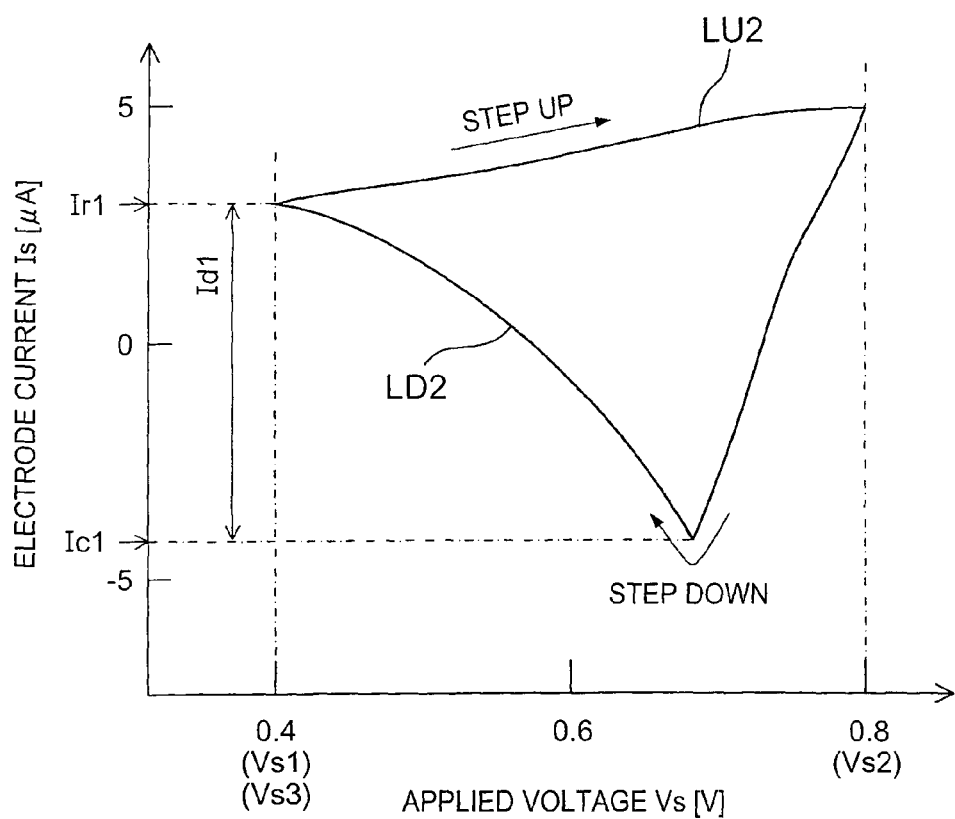
FIG. 7 is a graph that shows the correlation between an applied voltage and an electrode current at the time when the first control system according to the first embodiment has executed step-up operation and step-down operation.

At this time, as described above, SOx is reduced into sulfur (S), and the sulfur (S) is accumulated on the first cell cathode electrode 55A. Therefore, the electrode current Is at the time when the ECU 30 executes the step-up operation changes over a period of time T0 to time T1 at [B] in FIG. 6 as indicated by the curve LU2 in FIG. 7. That is, the electrode current Is gradually increases from time T0 to time T1.

When the step-up operation completes at time T1, the ECU 30 reduces the applied voltage Vs from the second voltage Vs2 (in this example, 0.8 V) to a third voltage Vs3 (in this example, 0.4 V) over a predetermined time. As a result, the applied voltage Vs reaches the third voltage Vs3 at time T2. Operation for reducing the applied voltage Vs, which is executed by the ECU 30, is also referred to as step-down operation. The third voltage Vs3 just needs to be a voltage lower than a voltage at which the entire sulfur (S) accumulated on the first cell cathode electrode 55A through the step-down operation is reoxidized and a voltage within the above-described limiting current region. In this example, the third voltage Vs3 is equal to the first voltage Vs1; however, the third voltage Vs3 may be a voltage different from the first voltage Vs1.

In a period (time T1 to time T2) in which the step-down operation is executed, sulfur (S) accumulated on the first cell cathode electrode 55A is reoxidized into SOx as described above. Therefore, the electrode current Is at which the ECU 30 executes the step-down operation changes in a period of time T1 to time T2 at [B] in FIG. 6 as indicated by the curve LD2 in FIG. 7. That is, the electrode current Is steeply decreases from time T1 in accordance with the step-down operation, once decreases to a local minimum value (specific current) Ic1, after that, starts increasing, and becomes a reference current Ir1 at time T2. The ECU 30 keeps the applied voltage Vs at the first voltage Vs1 until the next step-up operation is started.

A period from time T0 to time T1, that is, a period from the start of the step-up operation to the start of the step-down operation, is also referred to as first period for the sake of convenience. A period from time T1 to time T2, that is, a period in which the step-down operation is executed, is also referred to as second period for the sake of convenience.

Incidentally, the ECU 30 acquires the local minimum value (specific current) Ic1 during the step-down operation, and acquires the reference current Ir1 at the completion of the step-down operation. In addition, the ECU 30 obtains the current difference Id1 (Id1=Ir1−Ic1) that is a difference between the reference current Ir1 and the specific current Ic1, and provisionally acquires the concentration Csox of SOx by using the current difference Id1 and a map that expresses the correlation shown in FIG. 4. However, as described above, because the air-fuel ratio AF is fluctuating during the step-up operation (from time T0 to time T1), it is not possible to directly accurately obtain the concentration Cs of sulfur in fuel from the concentration Csox of SOx.

Therefore, the ECU 30 acquires the air-fuel ratio (actually, the air-fuel ratio of exhaust gas) with the use of the first cell 55 of the gas sensor 40 multiple times (in this example, ten times) during the step-up operation. Each of the acquired air-fuel ratios is denoted by AFs (s=1, 2, . . . , 10).

The ECU 30 calculates a correction coefficient Ks (s=1, 2, . . . , 10) corresponding to each of the air-fuel ratios AFs. The correction coefficient Ks is a coefficient for converting the concentration Csox of SOx, which is obtained in the case where the air-fuel ratio AFs during the step-up operation is a value AF1, to a corrected concentration Csoxm of SOx (second waveform characteristic value), which is obtained in the case where all the air-fuel ratios AFs during the step-up operation are a reference air-fuel ratio AFm (in this example, 20). The correction coefficient Ks will be described in detail later.

Figures 8, 9:
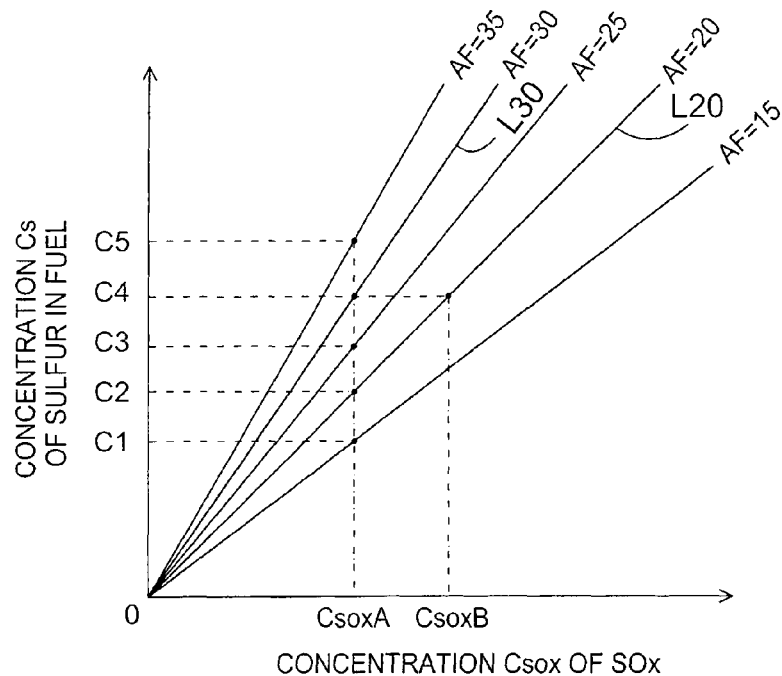
FIG. 8 is a graph that shows the correlation between a concentration of SOx in exhaust gas and a concentration of sulfur in fuel for each air-fuel ratio.
FIG. 9 is a table that shows a correspondence between an air-fuel ratio and a correction coefficient.

The ECU 30 corrects the provisionally acquired concentration Csox of SOx on the basis of the correction coefficient Ks (actually, an average correction coefficient Kave that is an average of the correction coefficients Ks), and applies the corrected concentration of SOx (corrected SOx concentration Csoxm) to the first correlation indicated by the straight line L20 in FIG. 8. Thus, the ECU 30 estimates the concentration Cs of sulfur in fuel. The first correlation is the correlation between the exhaust gas SOx concentration Csox (third waveform characteristic value) and the concentration Cs of sulfur in fuel, and the correlation is acquired in the case where the air-fuel ratio of exhaust gas during the step-up operation has been continuously the reference air-fuel ratio AFm. The first correlation is acquired through an experiment in advance, and is stored in the ROM 35 in map form.

The above-described correction coefficient Ks will be further described in detail. When the correlation between the air-fuel ratio AF and the exhaust gas SOx concentration Csox for each concentration Cs of sulfur in fuel as shown in FIG. 5 is expressed by the correlation between the concentration Csox of SOx and the concentration Cs of sulfur for each air-fuel ratio AF, the resultant correlation is shown in FIG. 8.

Assuming that the exhaust gas SOx concentration Csox obtained as described above (that is, obtained by using the current difference Id acquired through the step-up operation and the step-down operation, and the correlation shown in FIG. 4) is CsoxA. However, as is understood from FIG. 8, the concentration Cs of sulfur in fuel in the case where the air-fuel ratio AF in a step-up period is 15, 20, 25, 30 or 35 is respectively C1, C2, C3, C4 or C5. That is, as described above, even when the acquired concentration Csox of SOx is a certain specific value CsoxA, the actual concentration Cs of sulfur in fuel varies with the air-fuel ratio AF in the step-up period.

Therefore, the ECU 30 converts the obtained exhaust gas SOx concentration Csox to the exhaust gas SOx concentration Csox at the time when assuming that the air-fuel ratio AF in the step-up period is the reference air-fuel ratio AFm (in this example, 20) (that is, the corrected exhaust gas SOx concentration Csoxm) by using the correction coefficient Ks.

Specifically, as is understood from FIG. 8, for example, when the exhaust gas SOx concentration Csox obtained while the air-fuel ratio AF during the step-up operation is kept at 30 is the value CsoxA, the correction coefficient Ks is a coefficient for converting the value CsoxA to a value CsoxB. More specifically, in this example, it is defined that Ks=CsoxA/CsoxB, and the acquired exhaust gas SOx concentration Csox (=CsoxA) is divided by Ks (=CsoxA/CsoxB). Thus, the corrected concentration Csoxm of SOx (=CsoxB=Csox/Ks) is obtained. An example of such a correction coefficient Ks for each air-fuel ratio AF is shown in a table of FIG. 9. The table of FIG. 9 is stored in the ROM 35 in map form.

In addition, when the air-fuel ratio AF is kept at a constant value during the step-up operation, the ECU 30 is able to uniquely identify the correction coefficient Ks on the basis of the constant air-fuel ratio AF and the map shown in FIG. 9. However, actually, the air-fuel ratio AF momentarily fluctuates.

Therefore, as described above, the ECU 30 acquires the air-fuel ratio AF (actually the air-fuel ratio of exhaust gas) multiple times during the step-up operation, and acquires the correction coefficient Ks (s=1, 2, . . . , 10) corresponding to each of the plurality of (ten) acquired air-fuel ratios AFs by using the map shown in FIG. 9. In addition, the ECU 30 obtains the average of the plurality of (ten) correction coefficients Ks, and acquires the corrected SOx concentration Csoxm by correcting the exhaust gas SOx concentration Csox acquired by using the average (that is, average correction coefficient Kave). As described above, the ECU 30 estimates the concentration Cs of sulfur in fuel by using the corrected SOx concentration Csoxm and the first correlation indicated by the straight line L20 in FIG. 8. As a result, the first control system is able to accurately estimate the concentration Cs of sulfur in fuel without keeping the air-fuel ratio during the step-up operation at a constant value.

Next, the process of estimating the concentration Cs of sulfur (sulfur concentration estimation process), which is executed by the ECU 30, will be more specifically described with reference to the flowchart shown in FIG. 10. The CPU 34 (hereinafter, also simply referred to as CPU) of the ECU 30 starts the process from step 1000 each time a predetermined time elapses, and proceeds to step 1005.

In step 1005, the CPU determines whether the sulfur concentration estimation process is being executed.

Assuming that the sulfur concentration estimation process is not being executed or a request to start the process has not been issued. According to this assumption, the CPU makes negative determination in step 1005, proceeds to step 1010, and determines whether a request to start the sulfur concentration estimation process has been issued. According to the above-described assumption, because a request to start the sulfur concentration estimation process has not been issued, the CPU makes negative determination in step 1010, proceeds to step 1095, and once ends the routine.

A request to start the sulfur concentration estimation process is issued when the sulfur concentration estimation process has not been executed once after refueling. A request to start the sulfur concentration estimation process may be issued, for example, each time an accumulated value of an operation time of the engine 10 reaches a predetermined value or each time the vehicle on which the engine 10 is mounted travels a predetermined distance.

Next, assuming that a request to start the sulfur concentration estimation process has been issued when the sulfur concentration estimation process is not being executed. In this case, the CPU makes negative determination in step 1005, and proceeds to step 1010. The CPU makes affirmative determination in step 1010, and proceeds to step 1025.

In step 1025, the CPU determines whether it is the timing at which the air-fuel ratio AF (air-fuel ratio of exhaust gas) should be detected. As described above, in the first period, that is, in a period in which the applied voltage Vs is increased from the first voltage Vs1 (0.4 V) to the second voltage Vs2 (0.8 V), the CPU acquires the air-fuel ratio AF ten times. That is, the CPU acquires the air-fuel ratio AF1 to the air-fuel ratio AF10. More specifically, the CPU acquires the air-fuel ratio AF when the applied voltage Vs is equal to Vs1+{(Vs2−Vs1)/9}×n (where n=0, 1, 2, . . . , 9).

Because the present timing is just after the sulfur concentration estimation process is started, the applied voltage Vs is equal to Vs1=0.4 (V). Thus, the CPU makes affirmative determination in step 1025, and proceeds to step 1030.

In step 1030, the CPU detects the air-fuel ratio AF on the basis of the electrode current Ip of the first cell 55. The air-fuel ratio AF detected at this timing is stored in the RAM 36 as the air-fuel ratio AF1. Subsequently, the CPU proceeds to step 1035, acquires the correction coefficient Ks by consulting the table shown in FIG. 9, and stores the correction coefficient Ks in the RAM 36 as a correction coefficient Ks(1). That is, when the correction coefficient Ks acquired in step 1035 is a value obtained for the mth time after the sulfur concentration estimation process is started, the CPU stores the value in the RAM 36 as Ks(m). Subsequently, the CPU proceeds to step 1040, and increases the applied voltage Vs of the second cell 56 by a predetermined voltage ΔVu. That is, the CPU executes the step-up operation. Subsequently, the CPU proceeds to step 1095, and once ends the routine.

Next, assuming that the routine is executed while the step-up operation is being executed (that is, before completion of the step-up operation) and not at the timing at which the air-fuel ratio AF should be detected. According to this assumption, because the sulfur concentration estimation process is being executed, the CPU makes affirmative determination in step 1005, and proceeds to step 1015. The CPU makes affirmative determination in step 1015, and proceeds to step 1020. In step 1020, the CPU determines whether the applied voltage Vs is lower than or equal to the second voltage Vs2 (0.8 V). Thus, the CPU determines whether the step-up operation should be completed.

According to the above-described assumption, the applied voltage Vs is lower than or equal to the second voltage Vs2. Thus, the CPU makes affirmative determination in step 1020, and proceeds to step 1025 and the following steps. In step 1025, the CPU determines whether it is the timing at which the air-fuel ratio AF should be detected. According to the above-described assumption, because it is not the timing at which the CPU should detect the air-fuel ratio AF, the CPU makes negative determination in step 1025, proceeds to step 1040, and continues the step-up operation.

Next, assuming that the routine is executed while the step-up operation is being executed and when the timing at which the air-fuel ratio AF should be detected has come again. In this case, the CPU process to step 1025 via step 1000 to step 1020, and makes affirmative determination in step 1025. As a result, the air-fuel ratio AF is newly acquired and stored in the RAM 36 in step 1030, and the correction coefficient Ks is newly determined and stored in the RAM 36 as Ks(m) in step 1035. Through repetition of the above-described operations, the step-up operation is executed, and a plurality of (in this example, ten) correction coefficients Ks (Ks(m): m=1 to 10) are acquired.

Next, assuming that the routine is executed at completion of the step-up operation, that is, when the applied voltage Vs has reached the second voltage Vs2. In this case, the CPU makes negative determination in step 1020, proceeds to step 1045, and reduces the applied voltage Vs by a predetermined voltage ΔVd. That is, the CPU executes the step-down operation. The predetermined voltage ΔVd may be the same as the predetermined voltage ΔVu or may be different from the predetermined voltage ΔVu.

Subsequently, the CPU proceeds to step 1050, detects the electrode current Is of the second cell 56, and stores the electrode current Is in the RAM 36. The CPU proceeds to step 1055, and determines whether the step-down operation should be completed by determining whether the applied voltage Vs is lower than or equal to the third voltage Vs3 (0.4 V).

According to the above-described assumption, because the present timing is just after the step-down operation is started, the applied voltage Vs has not reached the third voltage Vs3. Thus, the CPU makes negative determination in step 1055, proceeds to step 1095, and once ends the routine.

Next, assuming that the routine is executed while the step-down operation is being executed (that is, before completion of the step-down operation). In this case, the CPU makes affirmative determination in step 1005, and proceeds to step 1015. The CPU makes negative determination in step 1015, and proceeds to step 1045 and step 1050. As a result, the applied voltage Vs is further reduced, and the electrode current Is is detected and stored in the RAM 36.

Next, assuming that the routine is executed at completion of the step-down operation, that is, when the applied voltage Vs has reached the third voltage. In this case, the CPU proceeds to step 1055 via step 1000, step 1015, step 1045 and step 1050, and makes affirmative determination in step 1055. As a result, the CPU proceeds to step 1060 to step 1075 that will be described below.

In step 1060, the CPU acquires the electrode current Is at the timing at which the step-down operation has completed, as the reference current Ir1. In step 1065, the CPU acquires the specific current Ic1 on the basis of the plurality of electrode currents Is detected through the repeatedly executed process of step 1050 and stored in the RAM 36 during the step-down operation. The specific current Ic1 is the local minimum value of the electrode current Is. In step 1070, the CPU obtains the current difference Id1 (that is, Difference Id1=Ir1−Ic1) that is a difference between the reference current Ir1 and the specific current Ic1, and provisionally acquires the concentration Csox of SOx by applying the current difference Id1 to the map (lookup table) shown in FIG. 4.

In step 1075, the CPU obtains the corrected SOx concentration Csoxm, and calculates the concentration Cs of sulfur in fuel on the basis of the corrected SOx concentration Csoxm. Specifically, the CPU calculates the average correction coefficient Kave that is the average of the correction coefficients Ks acquired during the step-up operation, and divides the concentration Csox of SOx by the average correction coefficient Kave. Thus, the corrected SOx concentration Csoxm is calculated (that is, Csoxm=Csox/Kave). The CPU acquires the concentration Cs of sulfur by applying the corrected SOx concentration Csoxm to the map (lookup table) that defines the first correlation indicated by the straight line L20 in FIG. 8.

Subsequently, the CPU proceeds to step 1080, and determines whether the concentration Cs of sulfur in fuel is smaller than a predetermined concentration threshold Csth1. When the concentration Cs of sulfur exceeds the concentration threshold Csth1, there is a possibility that sulfur in fuel causes degradation of the engine 10, generation of white smoke, or the like. In this case, there can occur a phenomenon (that is, sulfur poisoning) that sulfur and/or a sulfur compound adsorbs onto the surfaces of catalysts inside the exhaust gas control device 27, or the like, and, as a result, exhaust gas purification performance decreases.

Therefore, when the concentration Cs of sulfur has exceeded the concentration threshold Csth1, the CPU makes negative determination in step 1080, proceeds to step 1085, and informs a driver of the vehicle that the concentration Cs of sulfur in fuel is in a high state through lighting of an alarm lamp, beeping of an alarm sound, or the like, with the use of an informing device (not shown). The informing device is arranged at a driver seat of the vehicle on which the engine 10 is mounted. Subsequently, the CPU proceeds to step 1095, and ends the routine.

On the other hand, when the concentration Cs of sulfur has not exceeded the concentration threshold Csth1, the CPU determines that it is not required to provide the above information, that is, in this case, the CPU makes affirmative determination in step 1080, proceeds to step 1095, and ends the routine.

Although not shown in the drawings, the CPU constantly keeps the applied voltage Vp of the first cell 55 at a predetermined pump voltage Vpc. The limiting current region of the first cell 55 changes with a change in the air-fuel ratio AF. The pump voltage Vpc is set to a voltage that is included in the limiting current region within the range in which the air-fuel ratio AF changes during operation of the engine 10. Thus, the ECU 30 can detect the air-fuel ratio AF on the basis of the electrode current Ip of the first cell 55. In addition, the concentration of oxygen in the internal space 58 approaches zero, that is, almost the entire oxygen in the internal space 58 is removed through pumping. Thus, even when the air-fuel ratio AF changes during the step-down operation, the influence of the change in the air-fuel ratio AF almost does not appear in the waveform of the electrode current Is (that is, the waveform characteristic value).

As described above, the first control system includes the limiting current gas sensor (40) and the electronic control unit (ECU 30). The limiting current gas sensor (40) includes the pumping cell (second cell 56). The pumping cell (second cell 56) is arranged in the exhaust passage (exhaust passage 23) of the internal combustion engine (10). Exhaust gas in the exhaust passage is introduced to the pumping cell (second cell 56). The electronic control unit (ECU 30) executes the step-up operation for increasing the voltage (Vs) applied between the pair of electrodes (the second cell cathode electrode 56A and the second cell anode electrode 56B) of the pumping cell from the predetermined first voltage (Vs1) to the predetermined second voltage (Vs2) higher than the first voltage. The electronic control unit (ECU 30) executes the step-down operation for, after completion of the step-up operation, reducing the applied voltage from the second voltage to the predetermined third voltage (Vs3) lower than the second voltage. The electronic control unit is configured to acquire the air-fuel ratio (AF) of the exhaust gas multiple times in the first period (from time T0 to time T1) from the start of the step-up operation to the start of the step-down operation (step 1025 and step 1030 in FIG. 10). The electronic control unit is configured to acquire the waveform characteristic value (specific current Ic1) indicating the characteristic of the waveform of current flowing between the pair of electrodes in the second period (from time T1 to time T2) in which the step-down operation is executed (step 1060 to step 1070 in FIG. 10). The electronic control unit is configured to estimate an actual concentration of sulfur in fuel of the internal combustion engine by using the acquired waveform characteristic value and the plurality of acquired air-fuel ratios (AF) (step 1035, step 1070 and step 1075 in FIG. 10).

Figure 10:
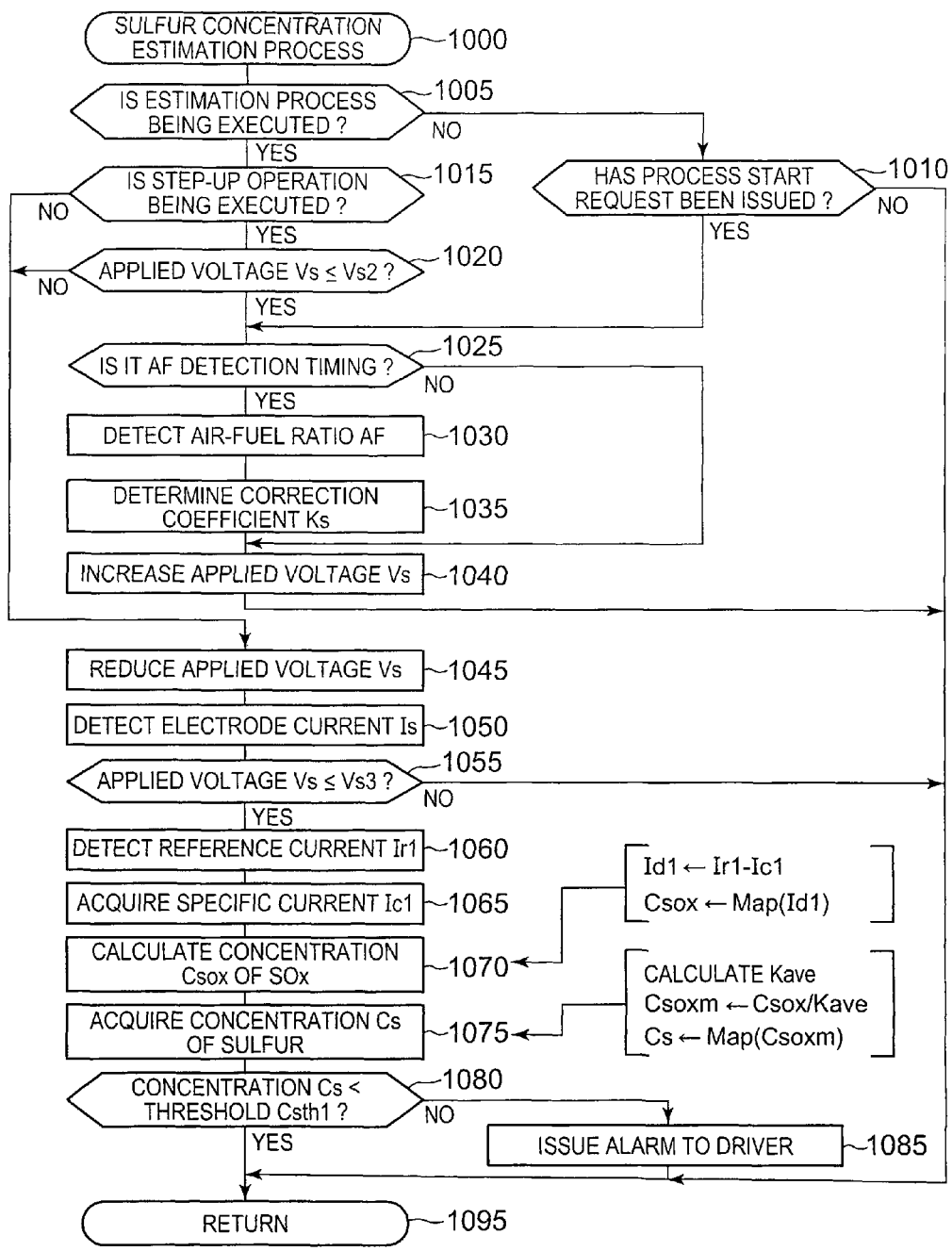
FIG. 10 is a flowchart that shows a sulfur concentration estimation process that is executed by the first control system according to the first embodiment.

The electronic control unit of the first control system is configured to, on the basis of the plurality of acquired air-fuel ratios, convert the acquired waveform characteristic value to a value according to a waveform characteristic value (corrected SOx concentration Csoxm) in the case where each of the plurality of acquired air-fuel ratios is assumed as the predetermined reference air-fuel ratio (AFm) (step 1070 and step 1075 in FIG. 10). The electronic control unit is configured to estimate an actual concentration of sulfur in the fuel on the basis of the value according to the converted waveform characteristic value and the first correlation (the straight line L20 in FIG. 8) between the value according to the waveform characteristic value and the concentration of sulfur in the fuel (step 1075 in FIG. 10). The first correlation is acquired in advance in the case where the air-fuel ratio of the exhaust gas in the first period has been continuously the reference air-fuel ratio.

The electronic control unit of the first control system employs the concentration of sulfur oxides in the exhaust gas (corrected SOx concentration Csoxm) as the value according to the waveform characteristic value (step 1075 in FIG. 10).

The electronic control unit of the first control system is configured to issue an alarm when the estimated concentration of sulfur is larger than the predetermined concentration threshold (step 1080 and step 1085 in FIG. 10).

The limiting current gas sensor of the first control system includes an oxygen removing unit (first cell 55) that is able to remove oxygen from exhaust gas that is introduced to the pumping cell (second cell 56). The electronic control unit is configured to remove oxygen from exhaust gas that is introduced to the pumping cell (second cell 56) within the second period (and within the first period) with the use of the oxygen removing unit.

Thus, with the first control system, even when the air-fuel ratio AF is not kept constant while the concentration Csox of SOx is being detected (that is, during a period in which the step-up operation or the step-down operation is executed, and at least during the step-up operation), it is possible to accurately detect the concentration of sulfur. As a result, it is possible to reflect the detected concentration of sulfur in control over the engine, use the detected concentration of sulfur in an alarm about a failure of the engine or put the detected concentration of sulfur to use in improvement of an on board diagnosis (OBD) on the exhaust gas control device.

Next, a control system (hereinafter, also referred to as second control system) for an internal combustion engine according to a second embodiment of the invention will be described. The engine 10 to which the first control system is applied includes the dual-cell limiting current gas sensor 40. In contrast, an engine 11 to which the second control system is applied includes an air-fuel ratio sensor 44 and a single-cell limiting current gas sensor 45, instead of the limiting current gas sensor 40. In addition, the first control system does not execute control for keeping the air-fuel ratio AF constant. In contrast, the second control system executes control for keeping the air-fuel ratio AF constant during the step-down operation. Hereinafter, these differences will be mainly described.

Figure 11:
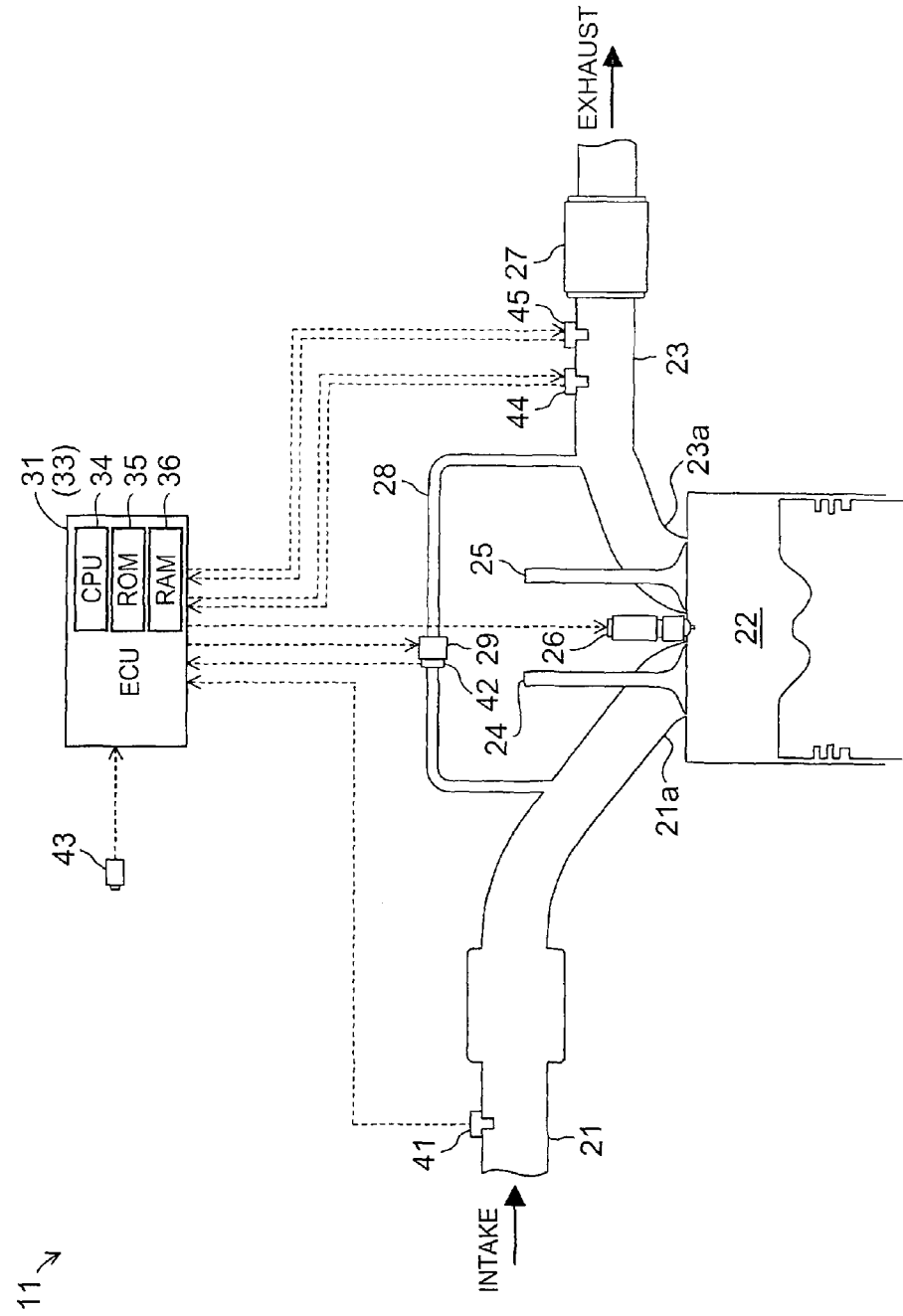
FIG. 11 is a schematic configuration view (cross-sectional view) of an internal combustion engine to which a control system (second control system) according to a second embodiment of the invention is applied.

The second control system is applied to the engine 11 of which the schematic configuration is shown in FIG. 11. In FIG. 11, like reference numerals denote the same members to those of the engine 10 shown in FIG. 1. The engine 11 includes the air-fuel ratio sensor 44 and the limiting current gas sensor 45. The air-fuel ratio sensor 44 and the gas sensor 45 are connected to the ECU 31.

The air-fuel ratio sensor 44 is a known limiting current air-fuel ratio sensor. The air-fuel ratio sensor 44 generates a signal indicating the air-fuel ratio AF. The air-fuel ratio sensor 44 includes similar components to those of the gas sensor 45 described in detail below.

Figure 12:
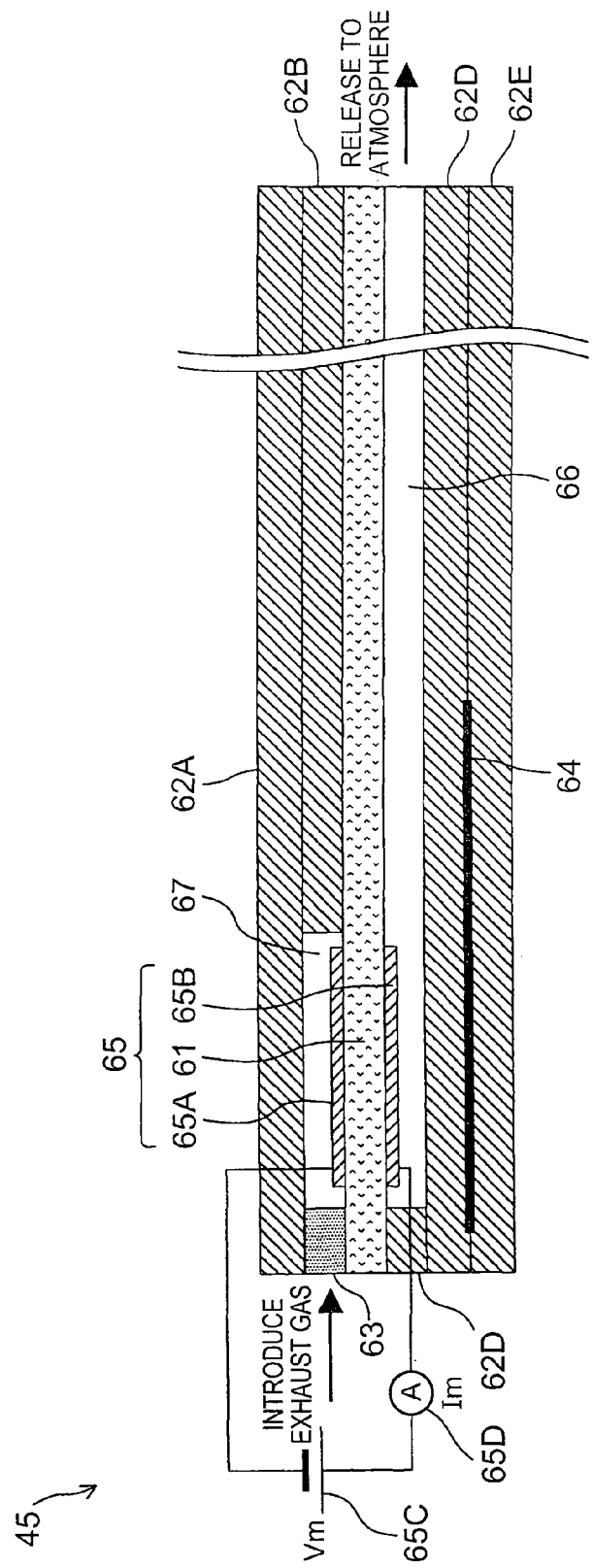
FIG. 12 is a schematic configuration view of a single-cell limiting current gas sensor included in the internal combustion engine to which the second control system according to the second embodiment is applied.

As shown in FIG. 12, the gas sensor 45 includes a solid electrolyte layer 61, a first alumina layer 62A, a second alumina layer 62B, a third alumina layer 62C, a fourth alumina layer 62D, a fifth alumina layer 62E, a diffusion-controlling layer (diffusion resistance layer) 63 and a heater 64.

The solid electrolyte layer 61 includes zirconia, or the like, and has an oxygen ion conductivity. The first to fifth alumina layers (62A to 62E) are dense (gas impermeable) layers containing alumina. The diffusion-controlling layer 63 is a porous layer, and is a gas permeable layer. The heater 64 is a heating element that is heated through energization.

The layers of the gas sensor 45 are laminated in order of the fifth alumina layer 62E, the fourth alumina layer 62D, the third alumina layer 62C, the solid electrolyte layer 61, the diffusion-controlling layer 63 and second alumina layer 62B, and the first alumina layer 62A from the lower side.

An atmosphere introduction passage 66 is a space that is defined by the solid electrolyte layer 61, the third alumina layer 62C and the fourth alumina layer 62D and that directly communicates with the outside atmosphere.

The internal space 67 is a space defined by the first alumina layer 62A, the solid electrolyte layer 61, the diffusion-controlling layer 63 and the second alumina layer 62B, and communicates with the inside of the exhaust passage 23 via the diffusion-controlling layer 63. Thus, when the pressure in the exhaust passage 23 is higher by a predetermined value or larger than the pressure in the internal space 67, exhaust gas in the exhaust passage 23 is introduced into the internal space 67 at a constant rate irrespective of the pressure in the exhaust passage 23. That is, the diffusion-controlling layer 63 is able to introduce exhaust gas in the exhaust passage 23 into the gas sensor 45 (internal space 67) while controlling the rate of exhaust gas. The heater 64 is arranged between the fourth alumina layer 62D and the fifth alumina layer 62E.

A first electrode 65A and a second electrode 65B are electrodes containing a platinum-group element, such as platinum and rhodium, or an alloy of the platinum-group element. The first electrode 65A is a cathode-side electrode. The second electrode 65B is an anode-side electrode.

The first electrode 65A is fixed to one-side surface of the solid electrolyte layer 61 (specifically, the surface of the solid electrolyte layer 61, which defines the internal space 67). The second electrode 65B is fixed to the other-side surface of the solid electrolyte layer 61 (specifically, the surface of the solid electrolyte layer 61, which defines the atmosphere introduction passage 66). The first electrode 65A, the second electrode 65B and the solid electrolyte layer 61 constitute a pumping cell 65.

A power supply 65C is able to apply an applied voltage (inter-electrode applied voltage) Vm to the first electrode 65A and the second electrode 65B. The applied voltage Vm is controlled by the ECU 31. An ammeter 65D generates a signal (voltage) that indicates an electrode current Im flowing through the pumping cell 65, and supplies the signal to the ECU 31.

The pumping cell 65, as well as the first cell 55 of the dual-cell limiting current gas sensor 40, is able to reduce SOx in exhaust gas into sulfur (S) when the applied voltage (inter-electrode applied voltage) Vm is increased, and to return the reduced sulfur (S) into SOx through reoxidation when the applied voltage Vm is reduced.

Figure 13:
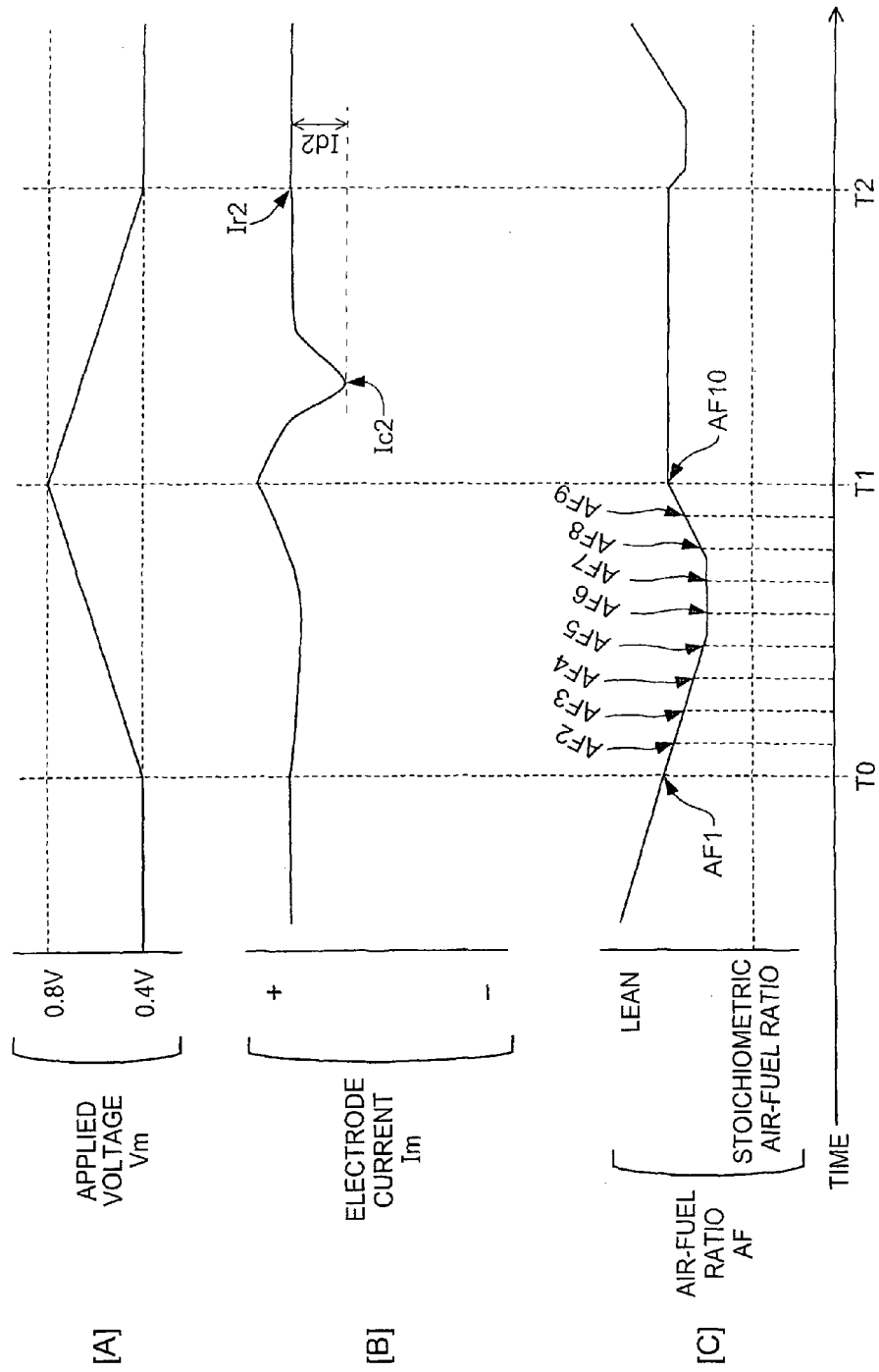
FIG. 13 is a time chart that shows temporal changes in applied voltage, electrode current and air-fuel ratio at the time when the second control system according to the second embodiment has executed step-up operation and step-down operation.
Figure 14:
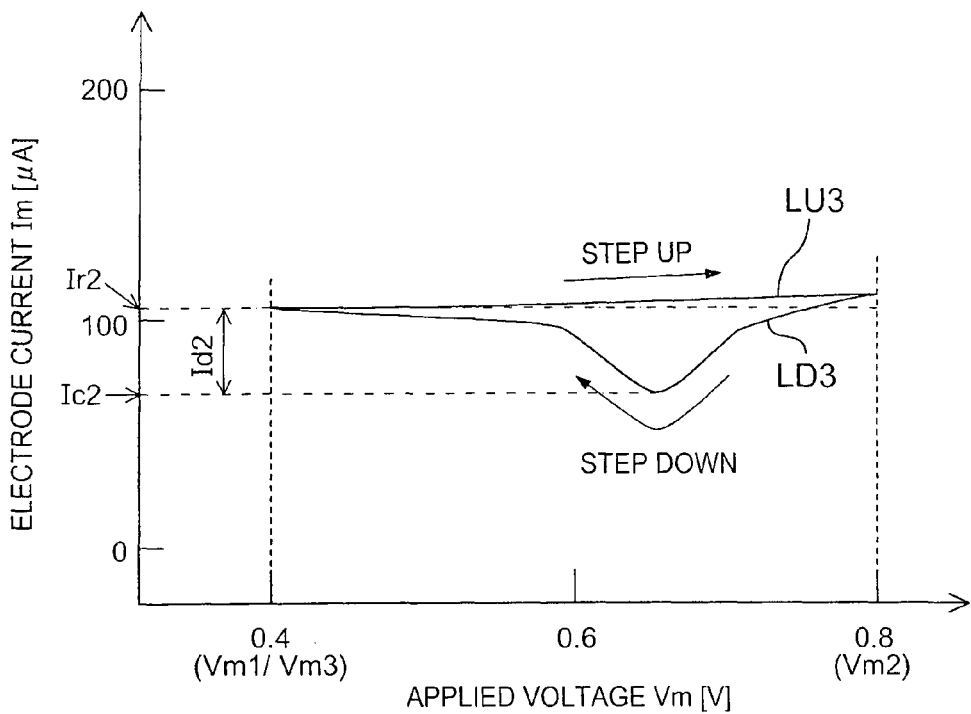
FIG. 14 is a graph that shows the correlation between an applied voltage and an electrode current at the time when the second control system according to the second embodiment has executed step-up operation and step-down operation.

In the second control system, the ECU 31 acquires the waveform characteristic value of the electrode current Im (a current difference Id2 shown in FIG. 13 and FIG. 14), the exhaust gas SOx concentration Csox and the concentration Cs of sulfur in fuel on the basis of a substantially similar principle to that of the first control system. However, in the second control system, the ECU 31 acquires the air-fuel ratio during the step-up operation on the basis of a signal from the air-fuel ratio sensor 44, and keeps the air-fuel ratio of the engine during the step-down operation at a constant value.

More specifically, when the concentration Csox of SOx is not detected (that is, in a period before time T0 in FIG. 13), the ECU 31 keeps the applied voltage Vm, which is applied to the gas sensor 45 (pumping cell 65), at a first voltage Vm1 (in this example, 0.4 V). The first voltage Vm1 is a voltage similar to the first voltage Vs1.

At the timing (time T0 in FIG. 13) at which the concentration Csox of SOx should be detected, the ECU 31 increases the applied voltage Vm from the first voltage Vm1 (in this example, 0.4 V) to a second voltage Vm2 (in this example, 0.8 V) over a predetermined time. As a result, the applied voltage Vm reaches the second voltage Vm2 at time T1. This operation is also referred to as step-up operation. The second voltage Vm2 is also a voltage similar to the second voltage Vs2.

During the step-up operation, SOx is reduced into sulfur (S), and the sulfur (S) is accumulated on the first electrode 65A. In this case, when the air-fuel ratio of exhaust gas does not change, current flowing through the pumping cell 65 because of decomposition (ionization) of oxygen is constant, so the electrode current Im is supposed to gradually increase because of reduction of SOx as indicated by the curve LU3 in FIG. 14. However, as shown in a period of time T0 to time T1 at [C] in FIG. 13, when the air-fuel ratio of exhaust gas changes during the step-up operation, the amount of current resulting from decomposition of oxygen changes with a change in the air-fuel ratio. Therefore, the electrode current Im at the time when the ECU 30 executes the step-up operation is not always limited to a gradual increase as shown in a period of time T0 to time T1 at [B] in FIG. 13.

When the step-up operation completes at time T1, the ECU 31 reduces the applied voltage Vm from the second voltage Vm2 (in this example, 0.8 V) to a third voltage Vm3 (in this example, 0.4 V) over a predetermined time. As a result, the applied voltage Vm reaches the third voltage Vm3 at time T2. This operation for reducing the applied voltage Vs is also referred to as step-down operation. The third voltage Vm3 is a voltage similar to the third voltage Vs3. In this example, the third voltage Vm3 is equal to the first voltage Vm1; however, the third voltage Vm3 may be a voltage different from the first voltage Vm1. In addition, the ECU 31 keeps the air-fuel ratio of the engine 11 at a constant value (in this example, the air-fuel ratio AF10 at the timing of completion of the step-up operation) in a period (from time T1 to time T2) of the step-down operation at [C] in FIG. 13.

In a period (from time T1 to time T2) of the step-down operation, sulfur (S) accumulated on the first electrode 65A is reoxidized into SOx as described above. Because the air-fuel ratio of the engine is kept at a constant value, current flowing through the pumping cell 65 because of decomposition (ionization) of oxygen is constant. Therefore, the electrode current Im at the time when the ECU 31 executes the step-down operation changes in a period of time T1 to time T2 at [B] in FIG. 13 as indicated by the curve LD3 in FIG. 14. That is, the electrode current Im steeply decreases from time T1 in accordance with the step-down operation, once decreases to a local minimum value (specific current) Ic2, after that, starts increasing, and becomes a reference current Ir2 at time T2. The ECU 31 keeps the applied voltage Vm at the first voltage Vm1 until the next step-up operation is started.

Figure 15:
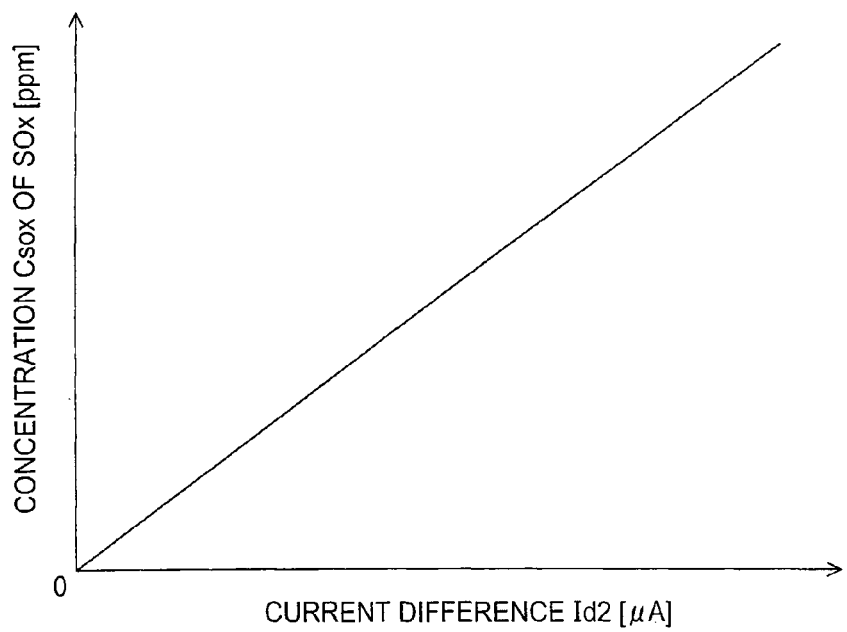
FIG. 15 is a graph that shows the correlation between a current difference and a concentration of SOx in exhaust gas.

In this way, the ECU 31 obtains a current difference Id2 (Id2=Ir2−Ic2) by executing the step-up operation and the step-down operation. In addition, the ECU 31 executes a correction process as well as the ECU 30 according to the first embodiment. That is, the ECU 31 acquires the air-fuel ratio AF multiple times (in this example, ten times) on the basis of a signal received from the air-fuel ratio sensor 44 during the step-up operation, acquires the correction coefficient Ks on the basis of the acquired air-fuel ratio AF, and calculates the average correction coefficient Kave on the basis of the plurality of correction coefficients Ks. The ECU 31 provisionally acquires the concentration Csox of SOx on the basis of the current difference Id2 and a map shown in FIG. 15, and converts the concentration Csox of SOx to the corrected SOx concentration Csoxm on the basis of the average correction coefficient Kave. After that, the ECU 31 acquires the concentration Cs of sulfur on the basis of the map (that is, the first correlation) indicated by the straight line L20 in FIG. 8 and the corrected SOx concentration Csoxm.

Next, the process of estimating the concentration Cs of sulfur (sulfur concentration estimation process), which is executed by the ECU 31, will be more specifically described with reference to the flowcharts shown in FIG. 16 and FIG. 17. Like step numbers denote step numbers of the steps already described with reference to FIG. 10 among steps shown in FIG. 16. The detailed description of these steps is omitted where appropriate. However, in FIG. 16, the applied voltage Vs is changed to the applied voltage Vm, and the electrode current Is is changed to the electrode current Im. In addition, the reference current Ir1, the specific current Id and the threshold Csth1 are respectively changed to the reference current Ir2, the specific current Ic2 and the threshold Csth2.

Figure 16:
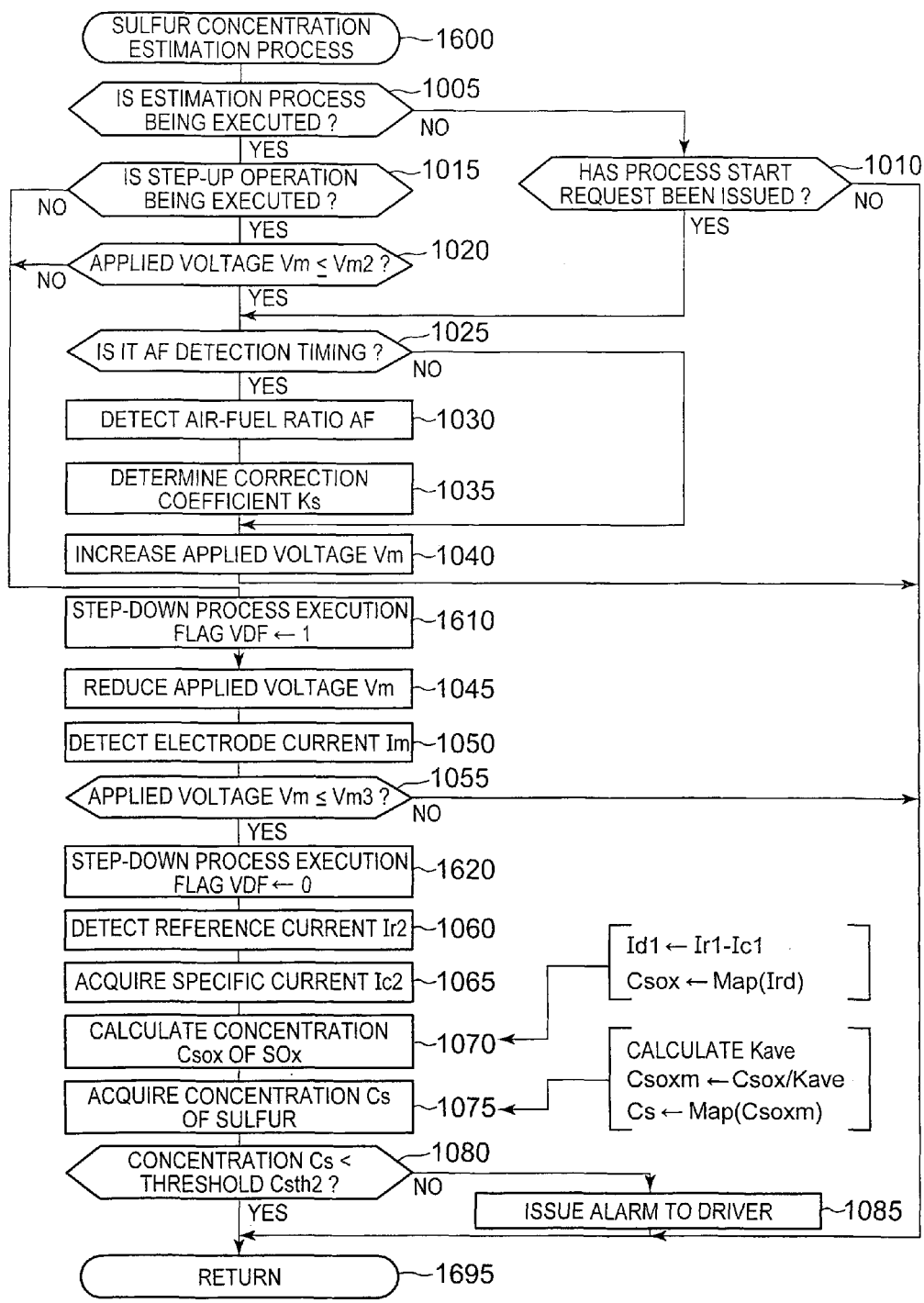
FIG. 16 is a flowchart that shows a sulfur concentration estimation process that is executed by the second control system according to the second embodiment.

The flowchart shown in FIG. 16 differs from the flowchart shown in FIG. 10 in that step 1610 and step 1620 are added in FIG. 16. This point will be described. The CPU of the ECU 31 proceeds to step 1610 at the timing at which the step-down operation is started (at the timing at which negative determination is made in step 1020), and sets the value of a step-down process execution flag VDf to 1 (on state). An initial value of the step-down process execution flag VDf is 0 (off state). The CPU proceeds to step 1620 at the timing at which the step-down operation is completed (at the timing at which affirmative determination is made in step 1055), and sets the value of the step-down process execution flag VDf to 0. As a result, the step-down process execution flag VDf is set to 1 when the CPU is executing the step-down process (that is, in the first period); and is set to 0 in the other case.

The step-down process execution flag VDf is used to execute the process of keeping the air-fuel ratio AF constant (air-fuel ratio keeping process). More specifically, the CPU executes the process shown in the flowchart of FIG. 17 each time a predetermined time elapses. Thus, the CPU starts the process from step 1700 at predetermined timing, proceeds to step 1705, and determines whether the step-down process execution flag VDf is 1.

When the CPU is executing the step-down process and the step-down process execution flag VDf is set to 1, the CPU makes affirmative determination in step 1705, proceeds to step 1710, and executes air-fuel ratio keeping control. More specifically, the CPU controls the fuel injection amount, the EGR valve open rate Er, and the like, so that the air-fuel ratio of the engine becomes a constant value (for example, the air-fuel ratio at the step-down process start timing). After that, the CPU proceeds to step 1795, and once ends the routine.

On the other hand, when the CPU is not executing the step-down process, the step-down process execution flag VDf is set to 0. Therefore, the CPU makes negative determination in step 1705, directly proceeds to step 1795, and once ends the routine. As a result, air-fuel ratio keeping control is not executed, and the air-fuel ratio is changed in accordance with the required air-fuel ratio and/or the engine operating state.

Figure 17:
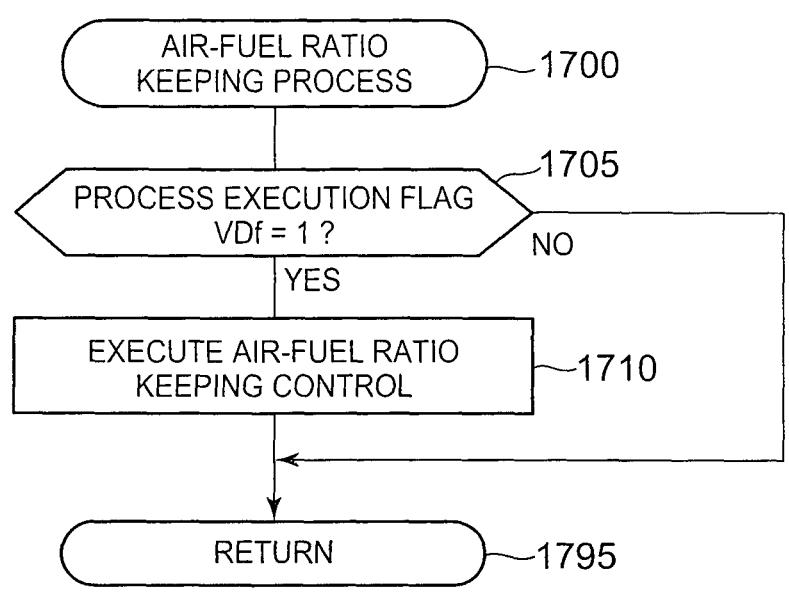
FIG. 17 is a flowchart that shows an air-fuel ratio keeping process that is executed by the second control system according to the second embodiment.

As described above, the electronic control unit (ECU 31) of the second control system is configured to control the internal combustion engine so that the air-fuel ratio (AF) of the exhaust gas is kept constant in the second period (from time T1 to time T2) (step 1610 and step 1620 in FIG. 16 and step 1710 in FIG. 17).

Thus, even in the case where the single-cell limiting current gas sensor 45 is used, the electrode current Im during the step-down operation does not receive the influence of the concentration of oxygen in exhaust gas. Therefore, it is possible to acquire the waveform characteristic value and the exhaust gas SOx concentration Csox, with the result that it is possible to further accurately detect the concentration of sulfur in fuel.

Next, a control system (hereinafter, also referred to as third control system) for an internal combustion engine according to a third embodiment of the invention will be described. The first control system estimates the concentration Cs of sulfur on the basis of the air-fuel ratios AF that are detected by the limiting current gas sensor 40 and the concentration Csox of SOx, and, when the estimated concentration Cs of sulfur exceeds the predetermined concentration threshold Csth1, informs the driver of the vehicle. In contrast, the third control system differs from the first control system only in that, when the average of the air-fuel ratios AF during the step-up operation, which are detected by the limiting current gas sensor 40, and the specific current Ic1 respectively satisfy predetermined conditions, the driver of the vehicle is informed. That is, the third control system informs the driver of the vehicle that the concentration Cs of sulfur is in a high state when the average of the air-fuel ratios during the step-up operation is larger than a predetermined air-fuel ratio threshold AFth and the specific current Ic1 is smaller than a predetermined current threshold Icth. Thus, the driver is allowed to take measures according to the above state. Hereinafter, this point will be mainly described.

As described above, as the concentration Cs of sulfur in fuel increases, that is, as the exhaust gas SOx concentration Csox increases, the specific current Ic1 decreases. On the other hand, even when the concentration Cs of sulfur is constant, the exhaust gas SOx concentration Csox increases as the air-fuel ratio of air-fuel mixture (that is, the air-fuel ratio AF of exhaust gas) during the step-up operation decreases. Thus, when the specific current Ic1 is smaller than the predetermined current threshold Icth (that is, Ic1<Icth) and the average (AFave) of the air-fuel ratios AF during the step-up operation is larger than the predetermined air-fuel ratio threshold AFth (that is, AFave>AFth), the concentration Cs of sulfur is higher than a predetermined value.

Therefore, instead of estimation of the concentration Cs of sulfur, when these conditions (that is, Ic1<Icth and AFave>AFth) are satisfied, the third control system informs the driver of the vehicle that the concentration Cs of sulfur is in a high state. These conditions are also referred to as predetermined conditions for the sake of convenience.

Next, a sulfur concentration informing process that is executed by an ECU 32 of the third control system will be specifically described with reference to the flowchart shown in FIG. 18. Like step numbers denote step numbers of the steps already described with reference to FIG. 10 among steps shown in FIG. 18. The detailed description of these steps is omitted where appropriate.

Figure 18:
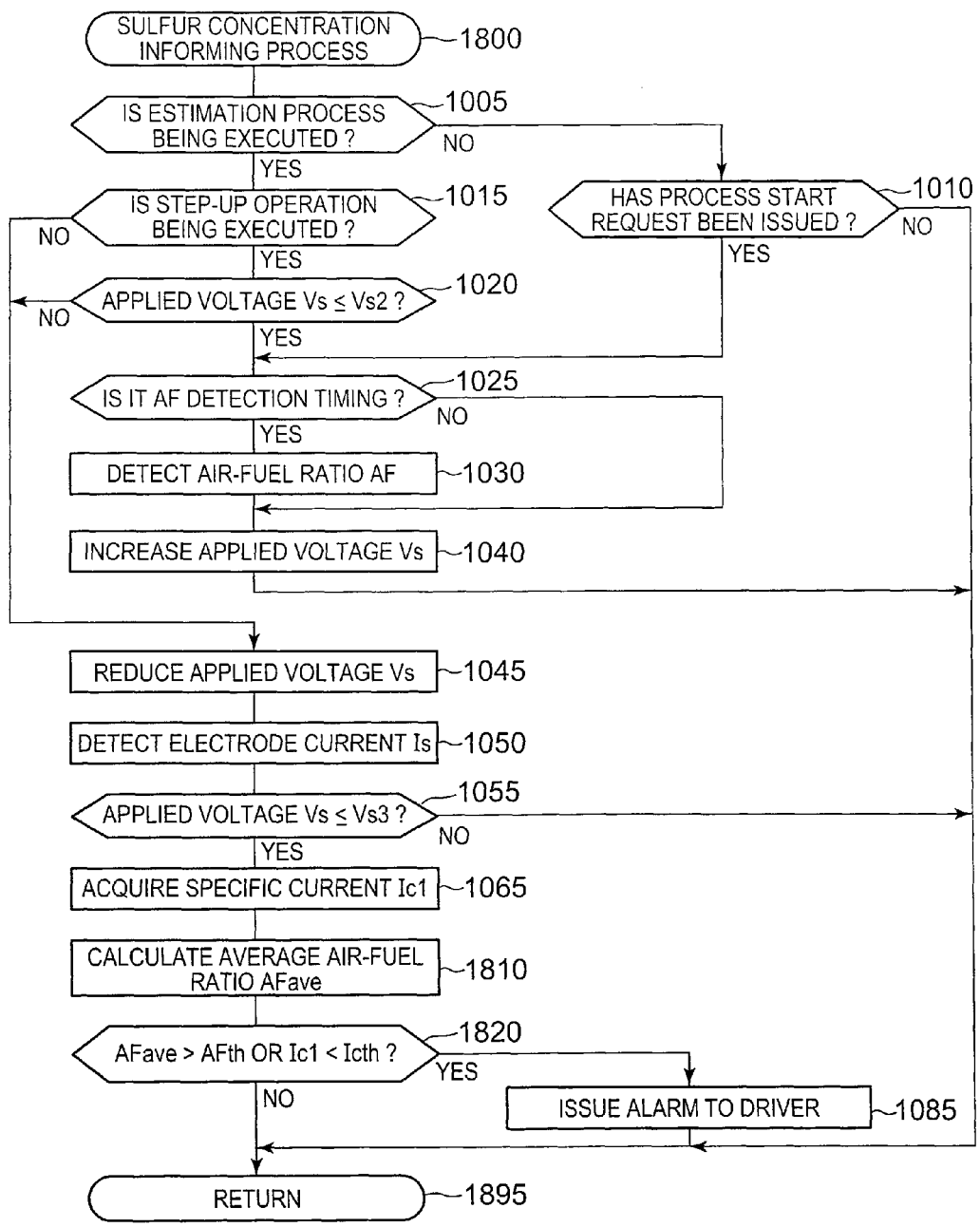
FIG. 18 is a flowchart that shows a sulfur concentration informing process that is executed by a control system according to a third embodiment of the invention.

The flowchart shown in FIG. 18 differs from the flowchart shown in FIG. 10 in that step 1035, step 1060 and step 1070 to step 1080 are omitted in FIG. 18 and step 1810 and step 1820 are added. This point will be descried. The CPU of the ECU 32 does not estimate the concentration Cs of sulfur, so the CPU does not need to execute any of step 1035, step 1060, and step 1070 to step 1080.

On the other hand, the CPU proceeds to step 1065 at the timing at which the step-down operation is completed (at the timing at which affirmative determination is made in step 1055), and subsequently proceeds to step 1810. In step 1810, the CPU calculates the average air-fuel ratio AFave that is the average of the plurality of air-fuel ratios AF acquired in step 1030 during the step-up operation. Subsequently, the CPU proceeds to step 1820, and determines whether the above-described predetermined conditions are not satisfied.

When the predetermined conditions are satisfied, the CPU makes affirmative determination in step 1820, proceeds to step 1085, and issues an alarm. On the other hand, when the predetermined conditions are not satisfied, the CPU makes negative determination in step 1820, proceeds to step 1895, and ends the routine.

As described above, the third control system includes the limiting current gas sensor (40) and the electronic control unit (ECU 32). The limiting current gas sensor (40) includes the pumping cell (second cell 56). The pumping cell (second cell 56) is arranged in the exhaust passage (exhaust passage 23) of the internal combustion engine (10). Exhaust gas in the exhaust passage is introduced to the pumping cell (second cell 56). The electronic control unit (ECU 32) executes the step-up operation for increasing the voltage (Vs) applied between the pair of electrodes (the second cell cathode electrode 56A and the second cell anode electrode 56B) of the pumping cell from the predetermined first voltage (Vs1) to the predetermined second voltage (Vs2) higher than the first voltage. The electronic control unit (ECU 32) executes the step-down operation for, after completion of the step-up operation, reducing the applied voltage from the second voltage to the predetermined third voltage (Vs3) lower than the second voltage. The electronic control unit is configured to acquire a step-up air-fuel ratio (average air-fuel ratio AFave) on the basis of the air-fuel ratios (AF) of the exhaust gas within the first period (from time T0 to time T1) from the start of the step-up operation to the start of the step-down operation (step 1030 and step 1810 in FIG. 18). The electronic control unit is configured to acquire the local minimum value of current (specific current Ic1) flowing between the pair of electrodes in the second period (from time T1 to time T2) in which the step-down operation is executed (step 1065 in FIG. 18). The electronic control unit is configured to issue an alarm when the acquired local minimum value and the acquired step-up air-fuel ratio respectively satisfy the predetermined conditions (step 1820 and step 1085 in FIG. 18).

The predetermined conditions are conditions that are satisfied when the acquired local minimum value (specific current Ic1) is smaller than the predetermined current threshold (Icth) and the acquired step-up air-fuel ratio (average air-fuel ratio AFave) is larger than the predetermined air-fuel ratio threshold (AFth).

The electronic control unit is configured to acquire the air-fuel ratio of the exhaust gas multiple times within the first period (step 1025 and step 1030 in FIG. 18), and employ the average of the plurality of acquired air-fuel ratios as the step-up air-fuel ratio (step 1810 in FIG. 18).

With the third control system, it is possible to provide information about the fact that the concentration Cs of sulfur in fuel is in a high state with a simple configuration.

Figure 19:
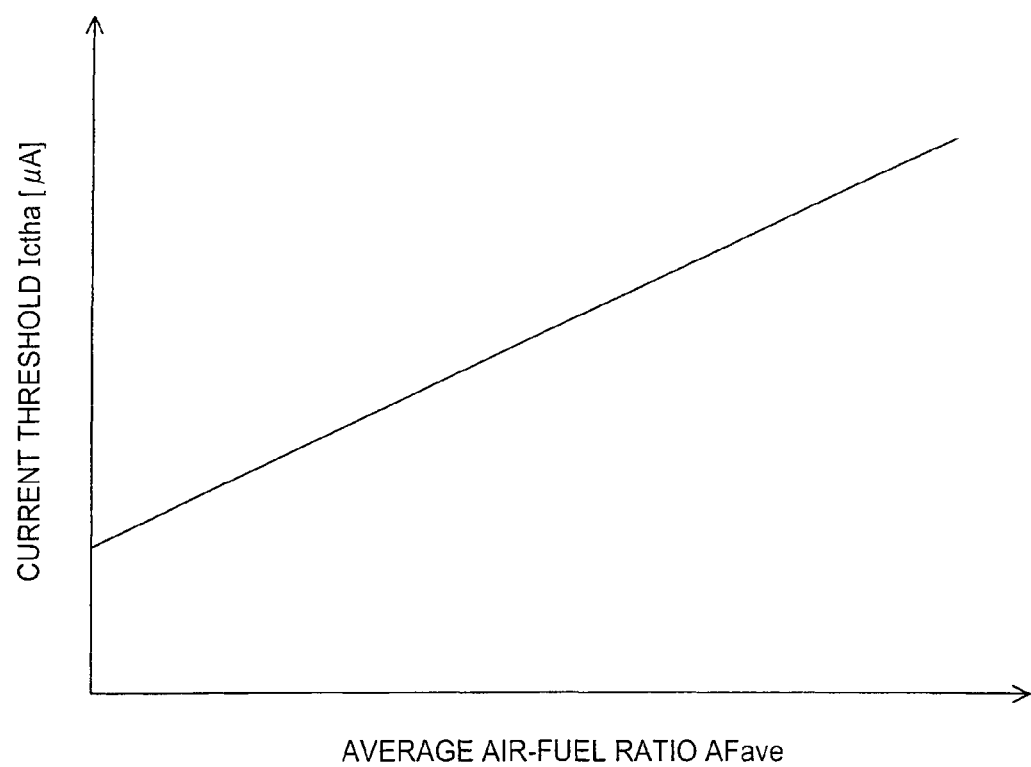
FIG. 19 is a graph that shows the correlation between an air-fuel ratio and a current threshold during step-up operation.

An alternative embodiment to the third embodiment will be described. As described above, even when the concentration Cs of sulfur in fuel is the same, but when the air-fuel ratio AF during the step-up operation is large, the exhaust gas SOx concentration Csox is small, so the specific current Ic1 is high. Thus, the CPU may set a current threshold Ictha to a value that increases as the average air-fuel ratio AFave increases as shown in FIG. 19, and may determine that the predetermined condition is satisfied when the specific current Ic1 is smaller than the current threshold Ictha.

In this alternative embodiment, the process of step 1820 in FIG. 18 differs from the above-described detail. More specifically, when the specific current Ic1 is smaller than the current threshold Ictha that is determined on the basis of the average air-fuel ratio AFave and the map that expresses the correlation shown in FIG. 19, the CPU makes affirmative determination in step 1820 of FIG. 18, and proceeds to step 1085. On the other hand, when the specific current Ic1 is larger than the current threshold Ictha, the CPU makes negative determination in step 1820 of FIG. 18, and proceeds to step 1895.

As described above, according to the above-described alternative embodiment, the predetermined condition is a condition that is satisfied when the acquired local minimum value (specific current Ic1) is smaller than the current threshold (current threshold Ictha) that increases as the acquired step-up air-fuel ratio (average air-fuel ratio AFave) increases (an alternative embodiment to the above-described step 1820 of FIG. 18).

Thus, according to the above alternative embodiment as well, it is possible to further accurately determine that the concentration Cs of sulfur in fuel is high with a simple configuration.

Next, a control system (hereinafter, also referred to as fourth control system) for an internal combustion engine according to a fourth embodiment of the invention will be described. The third control system is applied to the engine 10, while the fourth control system is applied to the engine 11. In addition, the second control system executes air-fuel ratio keeping control during the step-down operation so that the air-fuel ratio AF becomes equal to the air-fuel ratio at the start of the step-down operation. In contrast, the fourth control system executes reference air-fuel ratio keeping control during the step-down operation so that the air-fuel ratio AF becomes equal to the reference air-fuel ratio AFm. In addition, the second control system estimates the concentration Cs of sulfur by executing the correction process on the basis of the air-fuel ratio AFs and the current difference Id2 (=reference current Ir2−specific current Ic2), and informs the driver when the concentration Cs of sulfur is higher than the concentration threshold Csth2. On the other hand, the fourth control system, as in the case of the third embodiment, does not execute the correction process, and, when the average air-fuel ratio AFave and the specific current Ic2 satisfy the predetermined conditions, determines that the concentration Cs of sulfur is high, and informs the driver. Hereinafter, these differences will be mainly described.

As described above, when the single-cell limiting current gas sensor 45 is used, the reference current Ir2 increases as the air-fuel ratio AF during the step-down operation increases. However, in the fourth embodiment, as described above, the current difference Id2 is not calculated, and it is determined whether the concentration Cs of sulfur is high on the basis of the specific current Ic2 instead. Therefore, the fourth control system keeps the air-fuel ratio AF at the reference air-fuel ratio AFm (in this example, 20) during the step-down operation. Thus, it is possible to suppress a change in the reference current Ir2, so the specific current Ic2 has a one-to-one correlation with the concentration Csox of SOx.

Next, the sulfur concentration informing process that is executed by an ECU 33 of the fourth control system will be more specifically described with reference to the flowcharts shown in FIG. 20 and FIG. 21. Like step numbers denote step numbers of the steps already described with reference to any one of FIG. 10, FIG. 16 and FIG. 18 among steps shown in FIG. 20. In addition, like step numbers denote step numbers of the steps already described with reference to FIG. 17 among steps shown in FIG. 21. The detailed description of these steps is omitted where appropriate.

Figure 20:
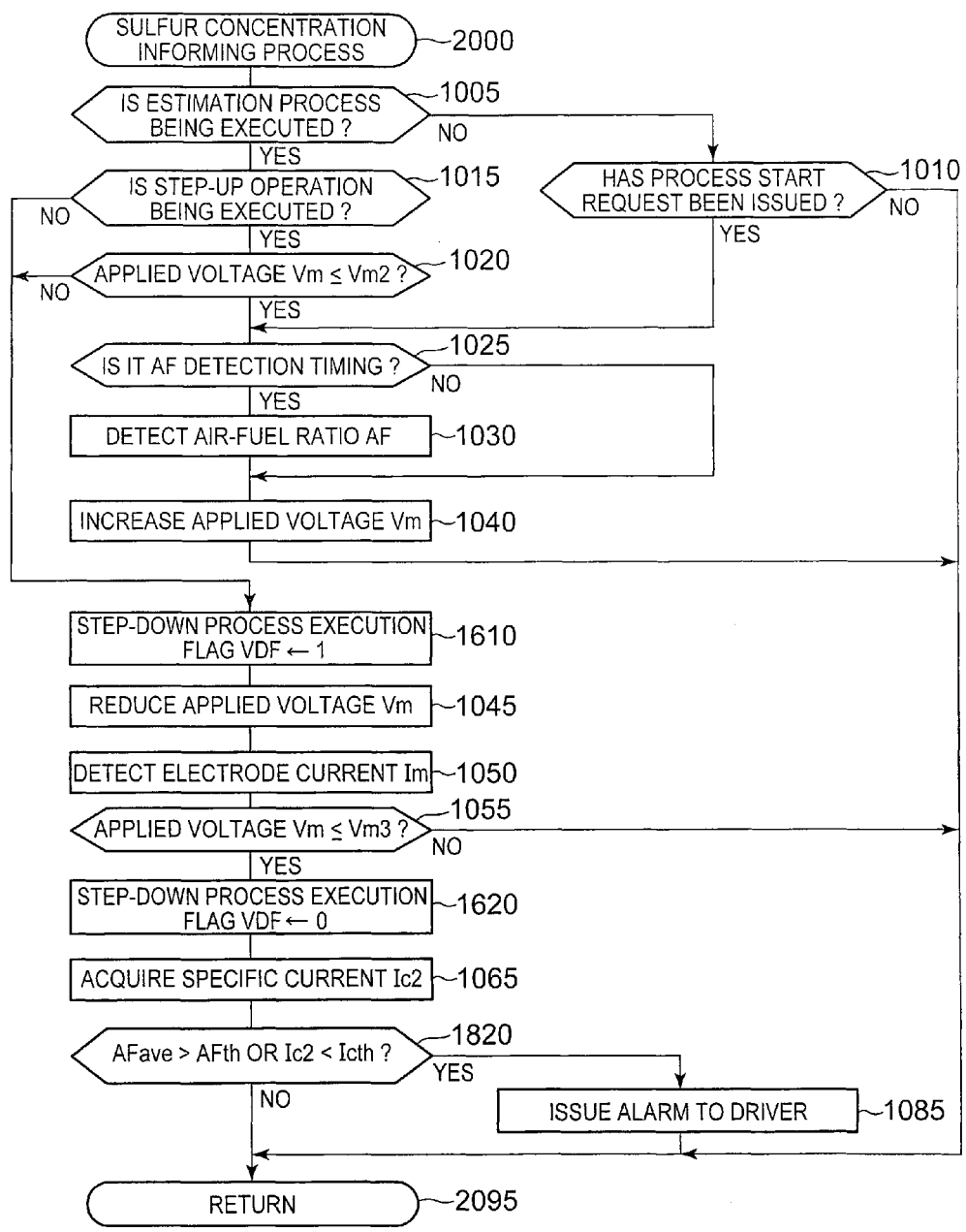
FIG. 20 is a flowchart that shows a sulfur concentration informing process that is executed by a control system (fourth control system) according to a fourth embodiment of the invention.

However, in FIG. 20, as compared to FIG. 18, the applied voltage Vs, the electrode current Is and the specific current Ic1 are respectively changed to the applied voltage Vm, the electrode current Im and the specific current Ic2. In addition, the flowchart shown in FIG. 20 differs from the flowchart shown in FIG. 18 in that step 1610 and step 1620 are added in FIG. 20. The flowchart shown in FIG. 21 differs from the flowchart shown in FIG. 17 in that step 2110 is executed instead of step 1710.

Figure 21:
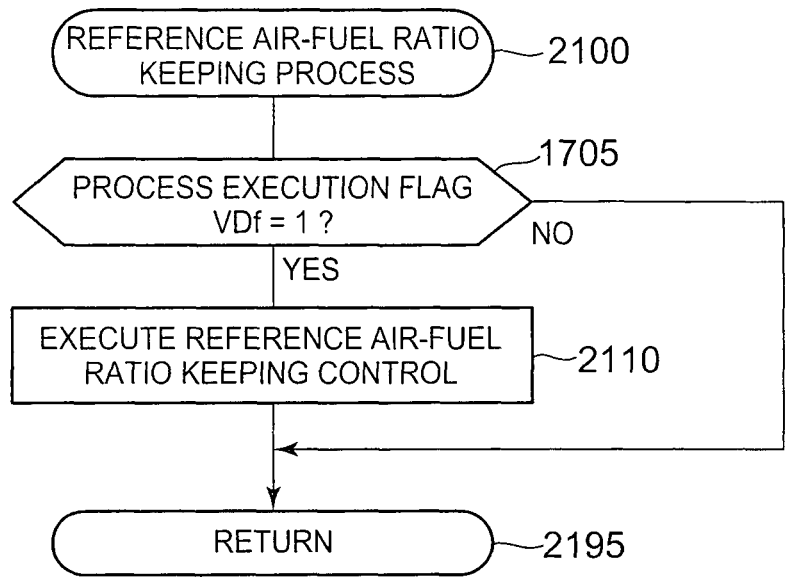
FIG. 21 is a flowchart that shows a reference air-fuel ratio keeping process that is executed by the fourth control system according to the fourth embodiment.

In FIG. 21, when affirmative determination is made in step 1705, that is, when the CPU 34 of the ECU 33 is executing the step-down process, the CPU proceeds to step 2110. In step 2110, the CPU executes reference air-fuel ratio keeping control. More specifically, as shown at [B] of FIG. 22, the CPU controls the fuel injection amount, the EGR valve open rate Er, and the like, during the step-down process (from time T1 to time T2) so that the air-fuel ratio AF becomes equal to the reference air-fuel ratio AFm. The air-fuel ratio AF may be kept constant during the step-down operation at another value different from the reference air-fuel ratio AFm.

Thus, with the fourth control system, it is possible to provide information about the fact that the concentration Cs of sulfur in fuel is in a high state with a simple configuration by using the single-cell limiting current gas sensor.

The embodiments of the control system for an internal combustion engine according to the invention are described above. However, the invention is not limited to the above-described embodiments. The invention may be modified in various forms without departing from the scope of the invention. For example, the invention not only encompasses a control system for an internal combustion engine, which is applied to a diesel engine, but also a control system for an internal combustion engine, which is applied to a gasoline engine.

In addition, the ECU according to each embodiment calculates the average correction coefficient Kave by averaging the correction coefficients Ks corresponding to the plurality of air-fuel ratios AF acquired during the step-up operation. However, each ECU may obtain the average of the plurality of air-fuel ratios AF acquired during the step-up operation, and may calculate the average correction coefficient Kave on the basis of the average and the lookup table shown in FIG. 9.

In addition, each of the ECUs according to the embodiments may calculate the average correction coefficient Kave not by an arithmetical mean of the correction coefficients Ks but by a weighted mean. In this case, each ECU may increase the weight as the air-fuel ratio AF is acquired later or each ECU may reduce the weight as the air-fuel ratio AF is acquired later.

In addition, each of the ECUs according to the first embodiment and the second embodiment employs the current difference Id1 or the current difference Id2 as the waveform characteristic value that indicates the characteristic of the waveform of the electrode current Is during the step-down operation (second period). However, each ECU may employ another value as the waveform characteristic value. For example, each ECU may employ the area of a region surrounded by a curve that is drawn as a result of a change in the electrode current Is during the step-down operation and a straight line that indicates the reference current Ir1 or the reference current Ir2 in the graph that indicates the electrode current Is for the applied voltage Vs, as the waveform characteristic value. In this case, each ECU estimates the concentration Csox of SOx as a higher value as the area (waveform characteristic value) increases. As the waveform characteristic value, the local minimum value Ic1 (specific current Ic1) or local minimum value Ic2 (specific current Ic2) of the electrode current Is may be employed.

Alternatively, each of the ECUs according to the first embodiment and the second embodiment may employ the magnitude (absolute value) of the amount of reduction in the electrode current Is (or the electrode current Im) per unit time (or unit voltage) from the start of the step-down operation to when the electrode current Is (or the electrode current Im) has reached the specific current Ic1 (or the specific current Ic2), as the waveform characteristic value. In this case, each ECU estimates the concentration Csox of SOx as a higher value as the magnitude of the amount of reduction (waveform characteristic value) increases.

In addition, the ECU according to each embodiment acquires the air-fuel ratio AF on the basis of the output of the gas sensor 40 or the air-fuel ratio sensor 44. However, each ECU may estimate the air-fuel ratio AF from the intake air amount Ga, the rotation speed NE, the fuel injection amount, and the like.

In addition, each of the engine 10 and the engine 11 according to the embodiments includes the EGR device. However, each engine does not need to include an EGR device. In this case, each of the ECUs according to the second embodiment and the fourth embodiment may use the fuel injection amount as a parameter for keeping the air-fuel ratio AF constant when air-fuel ratio keeping control (or reference air-fuel ratio keeping control) is executed.

In addition, each of the engine 10 and the engine 11 according to the embodiments does not include a throttle valve or a supercharger. However, each engine may include a throttle valve and/or a supercharger. In this case, each of the ECUs according to the second embodiment and the fourth embodiment may use a throttle opening degree and/or a supercharging pressure as a parameter for keeping the air-fuel ratio AF constant when air-fuel ratio keeping control (or reference air-fuel ratio keeping control) is executed.

In addition, the ECU according to each embodiment informs the driver of the vehicle when the concentration Cs of sulfur has exceeded the predetermined concentration threshold or the predetermined condition is satisfied, that is, when the specific condition is satisfied. However, each ECU may inform the driver of the vehicle when the duration of a state where the specific condition is satisfied has reached a predetermined period or when the total of a time during which the specific condition is satisfied has exceeded a predetermined temporal threshold.

In addition, the air-fuel ratio sensor 44 according to the second embodiment and the fourth embodiment is the limiting current air-fuel ratio sensor. However, as the air-fuel ratio sensor 44, another known air-fuel ratio sensor may be used as long as it is possible to obtain an output corresponding to the magnitude of the air-fuel ratio AF.

What is claimed is:

1. A control system for an internal combustion engine, the internal combustion engine including an exhaust passage and a limiting current gas sensor, the limiting current gas sensor including a pumping cell arranged in the exhaust passage, exhaust gas in the exhaust passage being introduced to the pumping cell, the control system comprising:
an electronic control unit configured to:
(i) execute step-up operation for increasing a voltage applied between a pair of electrodes of the pumping cell from a first voltage to a second voltage higher than the first voltage;
(ii) execute step-down operation for, after completion of the step-up operation, reducing an applied voltage from the second voltage to a third voltage lower than the second voltage;
(iii) acquire an air-fuel ratio of the exhaust gas multiple times within a first period from a start of the step-up operation to a start of the step-down operation;
(iv) acquire a first waveform characteristic value indicating a characteristic of a waveform of current flowing between the pair of electrodes within a second period in which the step-down operation is executed; and
(v) estimate an actual concentration of sulfur in fuel of the internal combustion engine by using the first waveform characteristic value and a plurality of acquired air-fuel ratios.

2. The control system according to claim 1, wherein
the electronic control unit is configured to acquire a local minimum value of current flowing between the pair of electrodes within the second period, as the first waveform characteristic value.

3. The control system according to claim 1, wherein
the electronic control unit is configured to convert the first waveform characteristic value to a first value according to a second waveform characteristic value based on the plurality of acquired air-fuel ratios, the second waveform characteristic value is a waveform characteristic value when each of the plurality of acquired air-fuel ratios is assumed as a predetermined reference air-fuel ratio,
the electronic control unit is configured to estimate the actual concentration of sulfur in the fuel based on the first value and a first correlation, and
the first correlation is a correlation between a second value according to a third waveform characteristic value and a concentration of sulfur in the fuel, and the third waveform characteristic value is a waveform characteristic acquired in advance when the air-fuel ratio of the exhaust gas has been continuously the reference air-fuel ratio within the first period.

4. The control system according to claim 3, wherein
the electronic control unit is configured to employ a concentration of sulfur oxide in the exhaust gas as the first value and the second value.

5. The control system according to claim 1, wherein
the electronic control unit is configured to issue an alarm when the estimated concentration of sulfur is larger than a predetermined concentration threshold.

6. A control system for an internal combustion engine, the internal combustion engine including an exhaust passage and a limiting current gas sensor, the limiting current gas sensor including a pumping cell arranged in the exhaust passage, exhaust gas in the exhaust passage being introduced to the pumping cell, the control system comprising:
an electronic control unit configured to:
(i) execute step-up operation for increasing a voltage applied between a pair of electrodes of the pumping cell from a first voltage to a second voltage higher than the first voltage;
(ii) execute step-down operation for, after completion of the step-up operation, reducing an applied voltage from the second voltage to a third voltage lower than the second voltage;
(iii) acquire a step-up air-fuel ratio based on an air-fuel ratio of the exhaust gas within a first period from a start of the step-up operation to a start of the step-down operation;
(iv) acquire a local minimum value of current flowing between the pair of electrodes within a second period in which the step-down operation is executed; and
(v) issue an alarm when the acquired local minimum value and the acquired step-up air-fuel ratio satisfy a predetermined condition.

7. The control system according to claim 6, wherein
the predetermined condition is a condition that is satisfied when the acquired local minimum value is smaller than a predetermined current threshold and the acquired step-up air-fuel ratio is larger than a predetermined air-fuel ratio threshold.

8. The control system according to claim 6, wherein
the predetermined condition is a condition that is satisfied when the acquired local minimum value is smaller than a current threshold that increases as the acquired step-up air-fuel ratio increases.

9. The control system according to claim 6, wherein
the electronic control unit is configured to acquire the air-fuel ratio of the exhaust gas multiple times within the first period, and
the electronic control unit is configured to employ an average of a plurality of acquired air-fuel ratios as the step-up air-fuel ratio.

10. The control system according to claim 1, wherein
the limiting current gas sensor further includes an oxygen removing unit that removes oxygen from exhaust gas that is introduced to the pumping cell, and
the electronic control unit is configured to remove oxygen from exhaust gas that is introduced to the pumping cell at least within the second period with the use of the oxygen removing unit.

11. The control system according to claim 10, wherein
the oxygen removing unit is another pumping cell different from the pumping cell, and
the electronic control unit is configured to acquire the air-fuel ratio of the exhaust gas based on current flowing between a pair of electrodes of the oxygen removing unit.

12. The control system according to claim 1, wherein the electronic control unit is configured to control the internal combustion engine such that the air-fuel ratio of the exhaust gas is kept constant within the second period.

13. A control method for an internal combustion engine, the internal combustion engine including an electronic control unit, an exhaust passage and a limiting current gas sensor, the limiting current gas sensor including a pumping cell arranged in the exhaust passage, exhaust gas in the exhaust passage being introduced to the pumping cell, the control method comprising:
- (i) executing, by the electronic control unit, step-up operation for increasing a voltage applied between a pair of electrodes of the pumping cell from a first voltage to a second voltage higher than the first voltage;
- (ii) executing, by the electronic control unit, step-down operation for, after completion of the step-up operation, reducing an applied voltage from the second voltage to a third voltage lower than the second voltage;
- (iii) acquiring, by the electronic control unit, an air-fuel ratio of the exhaust gas multiple times within a first period from a start of the step-up operation to a start of the step-down operation;
- (iv) acquiring, by the electronic control unit, a first waveform characteristic value indicating a characteristic of a waveform of current flowing between the pair of electrodes within a second period in which the step-down operation is executed; and
- (v) estimating, by the electronic control unit, an actual concentration of sulfur in fuel of the internal combustion engine by using the first waveform characteristic value and a plurality of acquired air-fuel ratios.

14. A control method for an internal combustion engine, the internal combustion engine including an electronic control unit, an exhaust passage and a limiting current gas sensor, the limiting current gas sensor including a pumping cell arranged in the exhaust passage, exhaust gas in the exhaust passage being introduced to the pumping cell, the control method comprising:
- (i) executing, by the electronic control unit, step-up operation for increasing a voltage applied between a pair of electrodes of the pumping cell from a first voltage to a second voltage higher than the first voltage;
- (ii) executing, by the electronic control unit, step-down operation for, after completion of the step-up operation, reducing an applied voltage from the second voltage to a third voltage lower than the second voltage;
- (iii) acquiring, by the electronic control unit, a step-up air-fuel ratio based on an air-fuel ratio of the exhaust gas within a first period from a start of the step-up operation to a start of the step-down operation;
- (iv) acquiring, by the electronic control unit, a local minimum value of current flowing between the pair of electrodes within a second period in which the step-down operation is executed; and
- (v) issuing, by the electronic control unit, an alarm when the acquired local minimum value and the acquired step-up air-fuel ratio satisfy a predetermined condition.

\* \* \* \* \*